US012590045B1

(12) United States Patent
Tanimu et al.

(10) Patent No.: US 12,590,045 B1
(45) Date of Patent: Mar. 31, 2026

(54) PROCESS FOR PRODUCING C2-C4 OLEFINS

(71) Applicant: KING FAHD UNIVERSITY OF PETROLEUM AND MINERALS, Dhahran (SA)

(72) Inventors: Abdulkadir Tanimu, Dhahran (SA); Abdullah Mohammed Aitani, Dhahran (SA); Ramzi Hadi Alshugaih, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 19/348,714

(22) Filed: Oct. 2, 2025

Related U.S. Application Data

(60) Provisional application No. 63/786,796, filed on Apr. 10, 2025.

(51) Int. Cl.
*C07C 4/06* (2006.01)
*C07C 4/22* (2006.01)

(52) U.S. Cl.
CPC ................. *C07C 4/06* (2013.01); *C07C 4/22* (2013.01); *C07C 2529/08* (2013.01); *C07C 2529/40* (2013.01)

(58) Field of Classification Search
CPC ......... C07C 4/06; C07C 4/22; C07C 2529/08; C07C 2529/40
See application file for complete search history.

(56) References Cited

U.S. PATENT DOCUMENTS

2013/0317271 A1    11/2013  Al-Ghrami et al.
2014/0228605 A1*   8/2014  Narayanaswamy ....... B01J 8/26
                                                585/241

(Continued)

FOREIGN PATENT DOCUMENTS

EP         3878926 A1      9/2021
WO       2023/111946       6/2023

OTHER PUBLICATIONS

Karagoz et al. ("Catalytic Coprocessing of Low-Density Polyethylene with VGO Using Metal Supported on Activated Carbon." Energy & Fuels 2002, 16, 1301-1308) (Year: 2002).*

(Continued)

*Primary Examiner* — In Suk C Bullock
*Assistant Examiner* — Jason Y Chong
(74) *Attorney, Agent, or Firm* — Oblon, McClelland, Maier & Neustadt, L.L.P.

(57) ABSTRACT

A process for producing $C_2$-$C_4$ olefins including the fluid catalytic cracking of a solution of a low-density polyethylene (LDPE) in a heavy vacuum gas oil in the presence of a catalyst, wherein the catalyst includes: an ultra-stable Y zeolite; and, a ZSM-5 zeolite, wherein the ZSM-5 zeolite has: a silica to alumina ratio by weight of from 40:1 to 80:1; a mesopore surface area of from 150 to 250 $m^2/g$, as determined by Barrett-Joyner-Halenda (BJH) desorption analysis; a mesopore volume of from 0.070 to 0.200 $cm^3/g$, as determined by Barrett-Joyner-Halenda (BJH) desorption analysis; and, a total acidity of from 0.25 to 0.75 mmol/g, as determined by ammonia temperature programmed desorption.

20 Claims, 23 Drawing Sheets

(56) References Cited

U.S. PATENT DOCUMENTS

| | | | |
|---|---|---|---|
| 2015/0190794 A1 | 7/2015 | Karthikeyani et al. | |
| 2020/0291306 A1* | 9/2020 | Aitani | B01J 29/80 |
| 2022/0041940 A1* | 2/2022 | Pradeep | C10G 11/182 |
| 2023/0085274 A1 | 3/2023 | Liu et al. | |
| 2023/0312863 A1* | 10/2023 | Timken | C10G 1/10 |

OTHER PUBLICATIONS

Atsushi Ishihara, et al., "Fundamental Study of the Preparation Method and Functions of Supported Metal Catalysts and Catalytic Matrices for Petroleum Refining", Journal of the Japan Petroleum Institute, vol. 67, Issue 01, 2024, pp. 1-14, 14 pages.
Kyong Hwan Lee, et al., "Catalytic degradation of waste HDPE over acidic catalysts with different pore sizes" Journal of Industrial and Engineering Chemistry, vol. 09, Issue 05, Sep. 2023, pp. 584-589, 1 Page, Abstract only.

* cited by examiner

| 11/21/2023 | HV | mag ⊞ | spot | WD | det | ○————— 5 μm —————○ |
|---|---|---|---|---|---|---|
| 3:37:14 PM | 20.00 kV | 10.000 x | 3.5 | 11.1 mm | ETD | |

| 11/21/2023 | HV | mag ⊞ | spot | WD | det | ○————— 1 μm —————○ |
|---|---|---|---|---|---|---|
| 3:36:03 PM | 20.00 kV | 50.000 x | 3.5 | 11.1 mm | CtS | |

| 11/21/2023 | HV | mag ⊞ | spot | WD | det | ○————— 5 µm —————○ |
|---|---|---|---|---|---|---|
| 3:42:27 PM | 20.00 kV | 10.000 x | 3.5 | 11.0 mm | ETD | |

| ✹ | 11/21/2023 | HV | mag ⊞ | spot | WD | det | ○————— 1 µm —————○ |
|---|---|---|---|---|---|---|---|
| | 3:41:05 PM | 20.00 kV | 50.000 x | 3.5 | 11.0 mm | ETD | |

| 11/21/2023 | HV | mag ⊞ | spot | WD | det | ○————— 5 μm —————○ |
| 3:41:18 PM | 20.00 kV | 15.000 x | 3.5 | 10.9 mm | ETD | |

—◇—HVGO ---□--- 2.5LDPE/HVGO —△-- 5LDPE/HVGO ----✳---- 10LDPE/HVGO

—◇—HVGO ---□--- 2.5LDPE/HVGO —△-- 5LDPE/HVGO ----✳---- 10LDPE/HVGO

PROCESS FOR PRODUCING C2-C4 OLEFINS

CROSS REFERENCE TO RELATED APPLICATION

The present application claims benefit of priority to U.S. Provisional Patent Application No. 63/786,796 having a filing date of Apr. 10, 2025, which is incorporated herein by reference in its entirety.

STATEMENT OF PRIOR DISCLOSURE BY INVENTOR

Aspects of the present disclosure are described in Tanimu et al. "Tuning the morphology and textural properties of ZSM-5 additive for co-cracking of waste plastics with vacuum gas oil to light olefins", Journal of Waste Management, Vol. 189:254-264 (2024), incorporated herein by reference in its entirety.

STATEMENT OF ACKNOWLEDGEMENT

Support provided by King Fahd University of Petroleum and Minerals (KFUPM) under Grant No. INRC2305 is gratefully acknowledged.

BACKGROUND

Technical Field

The present disclosure is directed to a process for producing C2-C4 olefins and, more particularly, relates to a process for producing C2-C4 olefins by fluid catalytic cracking (FCC) of a solution of low-density polyethylene (LDPE) in heavy vacuum gas oil (HVGO) in the presence of a zeolite catalyst.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

The importance of plastic goods, especially goods obtained from polyolefins, in fulfilling the fundamental needs of modern life is underestimated. On account of their versatility, low cost, and robustness, plastic materials have become extremely useful in diverse applications, from automobiles and agriculture, to construction and medicine. However, the robustness of plastics makes waste plastic disposal a serious environmental issue [See: Rahimi, A. R., Garciá, J. M., 2017. *Chemical recycling of waste plastics for new materials production. Nature Reviews Chemistry* 2017 1:6 1, 1-11. https://doi.org/10.1038/s41570-017-0046]. Given an average annual production of plastics of 430 million tonnes—about two-thirds of which is constituted by short-lived plastics which are to be used once and thrown away—a pragmatic approach for preventing the looming plastic waste crises must be sought [See: Geyer, R., Jambeck, J. R., Law, K. L., 2017. *Production, use, and fate of all plastics ever made. Sci Adv* 3].

Generally, waste landfills and incineration are discouraged worldwide on account of their harmful effects on the ecosystem [See: Pathak, G., Nichter, M., Hardon, A., Moyer, E., Latkar, A., Simbaya, J., Pakasi, D., Taqueban, E., Love, J., 2023. *Plastic pollution and the open burning of plastic wastes. Global Environmental Change* 80, 102648]. Thus, great attention is being given to innovative approaches to recycling plastic waste, especially chemical recycling-which commonly involves the depolymerization of the plastics to their constituent monomers—or converting the plastics into potentially useful intermediates, such as fuels and chemicals [See: Lovás, P., Hudec, P., Jambor, B., Hájeková, E., Horňáček, M., 2017. *Catalytic cracking of heavy fractions from the pyrolysis of waste HDPE and PP. Fuel* 203, 244-252].

Chemical recycling, otherwise defined as tertiary recycling, comprises thermal or catalytic cracking processes. While thermal cracking is a radical (random-chain scission) mechanism with no control of product distribution, catalytic cracking is product selective based on the catalyst properties and often requires a lower cracking temperature. Plastic waste pyrolysis is a further example of a chemical recycling process that has acquired reasonable technological development. Through plastic pyrolysis, direct fuel and chemical production is possible via simple and environmentally benign technologies [See: Amjad, U. e. S., Tajjamal, A., Ul-Hamid, A., Faisal, A., Zaidi, S. A. H., Sherin, L., Mir, A., Mustafa, M., Ahmad, N., Hussain, M., Park, Y. K., 2022. *Catalytic cracking of polystyrene pyrolysis oil: Effect of $Nb_2O_5$ and $NiO/Nb_2O_5$ catalyst on the liquid product composition. Waste Management* 141, 240-250]. Additionally, product selectivity can be obtained by modulating the pyrolysis operating conditions to yield a viable percentage of light olefins and aromatics.

Although waste plastic recycling technologies have advanced greatly, they have not been implemented commercially at large scale; most studies are limited to laboratory or pilot-plant scales. The main reason for this is considered to be the economic feasibility of constructing new refineries based on the new technologies and the challenges of additional processing of the formed products to suit their intended applications as automotive fuels or intermediate chemicals.

It is considered that a more viable recycling approach may be to utilize existing refinery setups, particularly existing fluid catalytic cracking (FCC) units, to co-crack plastic wastes together with other refinery streams, such as naphtha or vacuum gas oil (VGO). This approach is quite attractive since most of the constituent polymers of the plastics exhibit some dissolution in hydrocarbon mixtures. Moreover, refinery technologies are well established, such that there is little or no technical challenge in co-processing refinery streams with dissolved plastics. Additionally, the FCC technology has effectively converted HVGO and residues to chemicals [See: Tanimu, A., Tanimu, G., Alasiri, H., Aitani, A., 2022. *Catalytic Cracking of Crude Oil: Mini Review of Catalyst Formulations for Enhanced Selectivity to Light Olefins. Energy* & *Fuels* 36, 5152-5166]. Consequently, the co-cracking of plastic wastes with conventional refinery streams has been studied in different reactor designs, such as batch-reactors, fixed-bed reactors, and FCC riser reactors. This approach has been used for more than two decades, except that the choice of reactor design, catalyst formulations, and target product have changed over the years. For example, Ng (Ng, 1995) managed to increase the yield of transportation fuel from the catalytic co-cracking of 10 wt. % of high-density polyethylene (HDPE) with VGO in a fixed bed reactor loaded with KOB-627 catalyst; however, at 5 wt. % HDPE co-cracking, the naphtha produced from primary cracking was further cracked to gas and coke, thus decreasing the transportation fuel yield. Similarly, LDPE was recycled by co-cracking with VGO using a batch autoclave reactor and over an activated carbon-supported metal catalyst (M-Ac) at a temperature of from 425 to 450° C. to produce improved hydrocarbon fuel [See: Karagöz, S., Yanik, J., Uçar, S., Song, C., 2002. *Catalytic Coprocessing of Low-Density Polyethylene with VGO Using Metal Supported on Activated Carbon. Energy and Fuels* 16, 1301-1304]. In addition to co-cracking LDPE, the M-Ac acted as an effective hydrodesulfurization catalyst.

The co-processing of plastics with pure hydrocarbon solvents-such as toluene or benzene—has been considered an effective approach for studying the mechanism of plastic cracking; however, the low boiling point of pure hydrocarbon solvents has limited the plastic dissolution process, especially at high-loading [See: De La Puente, G., Klocker, C., Sedran, U., 2002. *Conversion of waste plastics into fuels: Recycling polyethylene in FCC. Appl. Catal. B* 36, 279-285]. Thus, a higher boiling point feedstock, such as VGO, light cycle oil (LCO), and heavy oils, are considered better solvents for the dissolution of plastic wastes [See: Arandes, J. M., Ereña, J., Azkoiti, M. J., Olazar, M., Bilbao, J., 2003. *Thermal recycling of polystyrene and polystyrene-butadiene dissolved in a light cycle oil. J. Anal. Appl. Pyrolysis* 70, 747-760]. VGO is mostly used as co-cracking feedstock with waste plastics or other feedstocks because it cracks better than the other high boiling point feeds [See: Tanimu, A., AlGhrami, M., Siddiqui, M. A. B., Aljishi, M. F., Aitani, A., Bahhar, M., 2024. *Steam catalytic cracking of vacuum gas oil: Effect of co-feeding naphtha or gas condensate on light olefins yield. Chemical Engineering Research and Design* 207, 392-403]. Although literature exists on the co-processing of plastics with VGO, the interest therein has always been on increasing the yield or improving the performance of liquid fuel.

With the ongoing refinery transition from being a major transportation fuel and fossil fuels energy producer to a petrochemicals and hydrogen producer, it is expected that the focus on co-processing plastics with VGO will shift towards improving the yield of petrochemicals instead of transportation fuel. Accordingly, one object of the present disclosure is to study the effects of catalytic co-processing of LDPE with heavy VGO (HVGO) on the yield of basic petrochemicals, specifically light olefins (ethylene and propylene).

SUMMARY

In an exemplary embodiment, a process for producing $C_2$-$C_4$ olefins is described. The process comprises fluid catalytic cracking of a solution of a low-density polyethylene (LDPE) in a heavy vacuum gas oil in the presence of a catalyst, wherein the catalyst comprises: an ultra-stable Y zeolite; and, a ZSM-5 zeolite, wherein the ZSM-5 zeolite has a silica to alumina ratio by weight of from about 40:1 to about 80:1, a mesopore surface area of from about 150 to about 250 m²/g, as determined by Barrett-Joyner-Halenda (BJH) desorption analysis, a mesopore volume of from about 0.070 to about 0.200 cm³/g, as determined by Barrett-Joyner-Halenda (BJH) desorption analysis, and a total acidity of from about 0.25 to about 0.75 mmol/g, as determined by ammonia temperature programmed desorption.

In some embodiments, the fluid catalytic cracking comprises: fluidizing a stream of the solution of the low density polyethylene (LDPE) in the heavy vacuum gas oil in a riser reactor; cracking the solution stream with the catalyst in the riser reactor to produce a cracked stream and spent catalyst; and, separating the cracked stream and the spent catalyst in a separator.

In some embodiments, the weight hourly velocity of the stream of the solution of the low density polyethylene (LDPE) in the heavy vacuum gas oil is from about 1 to about 20 hr$^{-1}$.

In some embodiments, the solution of the low density polyethylene (LDPE) in the heavy vacuum gas oil comprises from about 1 to about 15 wt. % of the low density polyethylene (LDPE), based on the total weight of the solution.

In some embodiments, the solution of the low density polyethylene (LDPE) in the heavy vacuum gas oil comprises from about 2 to about 15 wt. % of the low density polyethylene (LDPE), based on the total weight of the solution.

In some embodiments, the solution of the low density polyethylene (LDPE) in the heavy vacuum gas oil has a density of from about 0.85 to about 0.95 g/cm³.

In some embodiments, the solution of the low density polyethylene (LDPE) in the heavy vacuum gas oil has a density of about 0.89 to about 0.91 g/cm³.

In some embodiments, the solution of the low density polyethylene (LDPE) in the heavy vacuum gas oil has, based on the total weight of the solution, a carbon content of from about 85 to about 90 wt. %, and a hydrogen content of from about 10 to about 15 wt. %.

In some embodiments, the solution of the low density polyethylene (LDPE) in the heavy vacuum gas oil has: a sulfur content of from about 4000 to about 6000 parts per million by weight; and a nitrogen content of from about 150 to about 250 parts per million by weight.

In some embodiments, the fluid catalytic cracking is performed at a temperature of from about 500 to about 700° C.

In some embodiments, the fluid catalytic cracking is performed at a temperature of from about 550 to about 650° C.

In some embodiments, the ratio by weight of the catalyst to the solution is from about 3:1 to about 9:1.

In some embodiments, the ratio by weight of the catalyst to the solution is from about 4:1 to about 6:1.

In some embodiments, the catalyst comprises, based on the total weight of the catalyst, from about 80 to about 95 wt. % of the ultra-stable Y zeolite and from about 5 to about 20 wt. % of the ZSM-5 zeolite.

In some embodiments, the catalyst comprises, based on the total weight of the catalyst, from about 80 to about 90 wt. % of the ultra-stable Y zeolite and from about 10 to about 20 wt. % of the ZSM-5 zeolite.

In some embodiments, the ZSM-5 zeolite has a surface area of about 300 to about 400 m²/g, as determined by Brunauer-Emmett-Teller (BET) analysis.

In some embodiments, the ZSM-5 zeolite has, as determined by Barrett-Joyner-Halenda (BJH) desorption analysis, a mesopore surface area of from about 175 to about 250 m²/g and a mesopore volume of about 0.075 to about 0.200 cm³/g.

In some embodiments, the ZSM-5 zeolite has a median pore diameter of about 2 to about 6 nm, as determined by Barrett-Joyner-Halenda (BJH) desorption analysis.

In some embodiments, the ZSM-5 zeolite has a silica: alumina ratio by weight of about 50:1.

In some embodiments, the ZSM-5 zeolite has a silica: alumina ratio by weight of 75:1.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
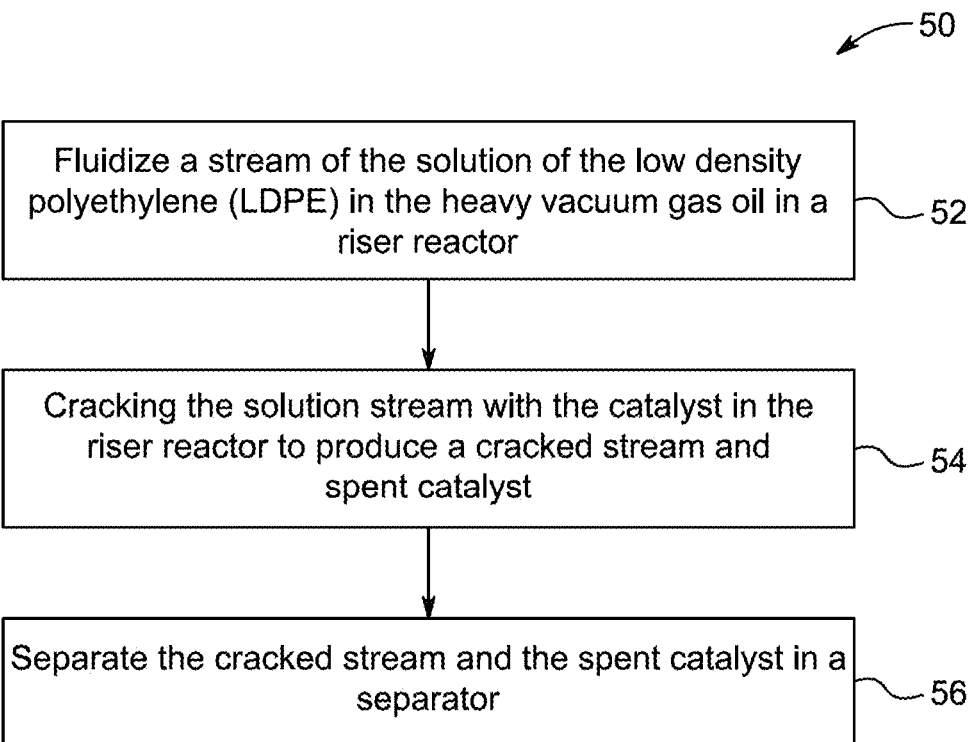
FIG. 1 is a flowchart of a process for producing $C_2$-$C_4$ olefins via a fluid catalytic cracking process, according to certain embodiments.

When describing the present disclosure, the terms used are to be construed in accordance with the following definitions, unless a context dictates otherwise.

As used herein, the words "a", "an" and the like generally carry a meaning of "one or more", unless stated otherwise.

Furthermore, the terms "approximately," "approximate", "about" and similar terms generally refer to ranges that include the identified value within a margin of 20%, 10%, or preferably 5%, and any values therebetween.

Embodiments of the present invention will now be described more fully hereinafter with reference to the accompanying drawings wherever applicable, in that some, but not all, embodiments of the disclosure are shown.

The word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

When amounts, concentrations, dimensions, and other parameters are expressed in the form of a range, a preferable range, an upper limit value, a lower limit value, or preferable upper and limit values, it should be understood that any ranges obtainable by combining any upper limit or preferable value with any lower limit or preferable value are also specifically disclosed, irrespective of whether the obtained ranges are clearly mentioned in the context.

In this application, a numerical value interval (i.e., a numerical value range) is involved, and, if not specifically stated, an optional numerical value distribution is considered continuous within the numerical value interval and includes two numerical value endpoints (i.e., minimum and maximum values) of the numerical value range and each numerical value between the two numerical value endpoints.

As used herein, the term 'fraction' refers to a numerical quantity which defines a part up to but not including 100 percent or the entirety of the thing in question.

The temperature parameters in the present application, if not specifically limited, are both allowed to be constant temperature processing and allowed to be varied within a certain temperature interval. It should be understood that the constant temperature processing allows the temperature to fluctuate within the precision range of the instrument control. It is allowed to fluctuate in the range of, for example, 5° C., 4° C., 3° C., 2° C., 1° C.

A weight percent of a component, unless specifically stated to the contrary, is based on the total weight of the formulation or composition in which the component is included. For example, if a particular element or component in a composition or article is said to have 5 weight percent (wt. %), it is understood that this percentage is in relation to a total compositional percentage of 100%.

The present disclosure is intended to include all hydration states of a given compound or formula, unless otherwise noted or when heating a material. For example, aluminum sulfate, $Al_2(SO_4)_3$, includes anhydrous $Al_2(SO_4)_3$, $Al_2(SO_4)_3 \cdot 18H_2O$, and any other hydrated forms or mixtures.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of nitrogen include $^{14}N$ and $^{15}N$. Isotopes of oxygen include $^{16}O$, $^{17}O$, and $^{18}O$. Isotopes of silicon include $^{28}Si$, $^{29}Si$, and $^{30}Si$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

The term "olefin" is used herein in accordance with its established meaning as an unsaturated hydrocarbon containing at least one carbon-carbon double bond. The term "$C_2$-$C_n$" olefin specifically references olefins having from 2 to n carbon atoms. In plural, the term "olefins" means a mixture comprising two or more unsaturated hydrocarbons containing at least one carbon-carbon double bond. In certain embodiments, the term "olefins" relates to a mixture comprising two or more of ethylene, propylene, butadiene, butylene-1 and isobutylene.

The term "low density polyethylene" (LDPE) as used herein refers to homopolymers of ethylene and copolymers of ethylene with up to 25% by weight of the reacted units of $C_3$ to $C_{20}$ α-olefin comonomer(s). Conventionally, the low density polyethylene will have a density in the range of from about 0.85 to about 0.95 g/cm³, as determined at 20° C. The low density polyethylene may, for instance, have a density of from about 0.87 to about 0.93 g/cm³, or from about 0.89 to about 0.91 g/cm³, as determined at 20° C.

As used herein, the term "vacuum gas oil" can include one or more $C_{22}$-$C_{52}$ hydrocarbons and boil in the range of from about 340 to about 590° C., for example from about 340 to about 560° C. at about 101.3 KPa. A vacuum gas oil may be a hydrocarbon product of vacuum distillation and be abbreviated herein to "VGO".

As used herein, the term "heavy vacuum gas oil" can include one or more $C_{36}$-$C_{52}$ hydrocarbons and boil in the range of from about 490 to about 590° C. or from about 340 to about 560° C. at about 101.3 KPa. The term "heavy vacuum gas oil" may be abbreviated herein to "HVGO".

As used herein the term "naphtha" refers to hydrocarbons boiling in the range of from about 20 to 205° C. The term is intended to encompass both: light naphtha, of which the hydrocarbons boil in the range of from about 20 to about 110° C.; and, heavy naphtha of which the hydrocarbons boil in the range of from about 110-205° C.

As used herein, the term "light cycle oil" (LCO) references the light cycle oil produced by fluid catalytic cracking unit: the distillation cut for this stream is conventionally in the range of from about 220 to about 330° C.

The term "heavy cycle oil" (HCO) references the heavy cycle oil which is produced by fluid catalytic cracking units: the distillation cut for this stream is conventionally in the range of from about 330 to about 510° C.

The term "cycle oil" may be used herein to refer to a mixture of LCO and HCO.

The term "catalytic cracking" refers to a process of refining of a hydrocarbon-based feedstock using high temperature and relatively low pressure in the presence of a catalyst, as a result of which heavy and relatively complex hydrocarbons that are present in feedstock are broken down into simpler and lighter hydrocarbons.

The term "fluid catalytic cracking" or "FCC" refers herein to a type of catalytic cracking, which employs a catalyst, typically in a form of a powder, having the particles suspended in a rising flow of feed hydrocarbons to form a fluidized bed. The abbreviation "FCC" may also refers, where applicable, to the apparatus, such as a fluidized catalytic cracking reactor, where the process of fluid catalytic cracking is carried out.

As used herein, the term 'fluid catalytic cracking (FCC) catalyst' refers to a substance used in the FCC process. These catalysts typically consist of solid materials, often zeolites, that facilitate the chemical reactions needed to crack large molecules into lighter ones.

As used herein the term "weight hourly space velocity" (WHSV) references the weight of feed flowing per unit weight of the catalyst per hour. Where the weight of the catalyst charged into a reactor is not varied, so any variation in flow of liquid per hour into the reactor will change the WHSV. The inverse of the weight hourly space velocity is the contact time, that is how much time the liquid is in contact with the catalyst under the conditions of operation.

As used herein, the term "zeolite" refers to a natural or synthetic aluminosilicate molecular sieve having a framework constructed of alumina ($AlO_4$) and silica ($SiO_4$). Adjacent tetrahedra are linked at their corners via a common oxygen atom, which results in an inorganic macromolecule with a three-dimensional framework. The three-dimensional framework of a zeolite also comprises channels, channel intersections, and/or cages having dimensions in the range of 0.1-10 nm, preferably 0.2-5 nm, more preferably 0.2-2 nm. Water molecules may be present inside these channels, channel intersections, and/or cages. The zeolite has the ability to be dehydrated without experiencing significant changes in the crystalline structure.

The term "equilibrium catalyst" or "Ecat" is used herein to indicate the inventory of circulating fluid cracking catalyst composition in an FCC unit operating under catalytic cracking conditions.

The term "ultra-stable Y zeolite" (USY zeolite) refers to a dealuminated form of a Y-type zeolite which may typically have an Si:Al ratio of at least about 6. There is no particular intention to limit the method by which ultra-stable Y (USY) zeolites having utility in the present disclosure may be obtained or synthesized. Such zeolites are, however, conventionally formed by a process that involves either steaming or acid leaching of Y-zeolites to remove aluminum from the framework, leading to a more stable and modified structure. Steam hydrolyzes the Al—O—Si bonds of the Y zeolite, causing some aluminum to be expelled from the framework. Moreover, exemplary acids having utility in leaching include, but are not limited to citric acid, nitric acid and hydrochloric acid.

The term "ultra-stable Y zeolite" is intended to encompass unexchanged ultra-stable Y-zeolites and ion-exchanged ultra-stable Y zeolites, such as rare-earth exchanged ultra-stable Y-zeolites (REUSY). Ion-exchanged zeolites are conventionally prepared by either: (a) acid treatment of the ultra-stable Y zeolite at a set pH, followed by ion exchange; or, (b) exchanging the ultra-stable Y zeolite with an acidic solution of a chloride salt of the metal to be exchanged.

For purposes of the present invention, the Si/Al ratio refers to the Si/Al atomic ratio of the overall crystalline zeolite material and not just of the MFI framework.

As used herein, the term 'porosity' refers to a measure of the void or vacant spaces within a material.

As used herein, the term 'pore diameter' may be thought of as the length or longest dimension of a pore opening.

As used herein, the term 'pore volume' refers to the total volume of the empty spaces, or pores, within a material.

As used herein, the Brunauer-Emmett-Teller (BET) analysis references the method of measuring the specific surface area ($m^2/g$) of a solid material via the adsorption of gas molecules onto the surface of the solid, as detailed in standard NF ISO 5794-1, Appendix E (June 2010).

As used herein, the Barrett, Joyner, and Halenda (BJH) desorption analysis refers to the method of determining the volume of mesopores per unit mass (mL/g) of a solid material utilizing the adsorption and desorption isotherms associated with gas molecules inside the mesopores of the solid, as detailed in Technical Standard DIN 66134:1998-02.

The term 'dropwise' as used herein means that one discrete drop or aliquot of a liquid, irrespective of its size or volume, is administered at a time. Discrete drops or aliquots are administered consecutively: they may be provided at regular intervals, at irregular intervals or both such intervals may be applied over the course of administration of the liquid. Further, the volume of an aliquot or drop may be independently determined and thus may be varied over the course of administration of the liquid. Exemplary devices for dropwise addition of liquids include syringes and columns.

As used herein, the term 'gel' refers to a viscoelastic or semi-solid phase that may form when a sol undergoes a transition to a more structured, three-dimensional network. This transition may occur through polymerization or cross-linking, typically facilitated by the addition of a gelling agent or by partial evaporation of the liquid medium of the sol. The result is a gel in which the liquid phase is entrapped within a solid network, creating a material that is free-standing or self-supporting—in that its yield value is greater than the sheer stress imposed by gravity—but which is still composed of a significant amount of liquid.

The term 'hydrothermally heating' as used herein refers to a method of heating which utilizes $H_2O$ as a heat transfer medium.

Where the terms "dry" or "drying" are used in the context of a method step in the present disclosure, this is intended to encompass the removal of any compound or composition which is in liquid form when measured at 25° C. under ambient conditions. The dry or dried material may comprise less than about 5 wt. %, for example less than about 3 wt. %, less than about 2 wt. %, less than about 1%, or even about 0% of said compound or composition being in liquid form when measured at 25° C. under ambient conditions. Exemplary such compounds or compositions include water, oils, organic solvents and other wetting agents.

As used herein, the term 'calcination' refers to a thermal treatment process which is conducted in the absence of, or under a restricted supply of ambient oxygen. This is performed to remove impurities or volatile substances and/or to induce thermal decomposition or a change in the thermally treated material.

As used herein, '$C_1$-$C_n$ alkyl' group refers to a monovalent group that contains from 1 to n carbons atoms, that is a radical of an alkane and includes straight-chain and branched organic groups. As such, a '$C_1$-$C_4$ alkyl' group refers to a monovalent group that contains from 1 to 4 carbons atoms, that is a radical of an alkane and includes straight-chain and branched organic groups. Examples of alkyl groups include, but are not limited to: methyl; ethyl; propyl; isopropyl; n-butyl; isobutyl; sec-butyl; and, tert-butyl. In the present disclosure, such alkyl groups may be unsubstituted or may be substituted with one or more halogen. Where applicable for a given moiety (R), a tolerance for one or more non-halogen substituents within an alkyl group will be noted in the specification.

It is noted that references in the specification to "an embodiment", "some embodiments", "other embodiments" or the like indicate that the embodiment(s) described may include a particular feature, structure, or characteristic, but every embodiment may not necessarily include that particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement the described embodiment(s).

Aspects of the present disclosure are directed to a zeolite catalyst for fluid catalytic cracking (FCC) of low-density polyethylene (LDPE) and heavy vacuum gas oil (HVGO) to produce light olefins ($C_2$ to $C_4$). For this purpose, three ZSM-5 zeolites with varying Si/Al ratios, specifically 25 (ZSM-5(25)), 50 (ZSM-5(50)) and 75 (ZSM-5(75)) were synthesized and combined with equilibrium catalyst (E-Cat)—which herein comprises or consists of an ultra-stable Y (USY) zeolite—to form E-Cat/ZSM-5(25), E-Cat/ZSM-5(50) and E-Cat/ZSM-5(75) respectively. The prepared catalysts were evaluated for their potential in FCC of a mixture of dissolved LDPE and HVGO to light olefins. The results indicate that the E-Cat/ZSM-5(50) has slightly better endothermic conversion (cracking) of the mixture of dissolved LDPE and HVGO into $H_2$, $C_1$ to $C_4$ gases and $C_2$-$C_4$ light olefins compared to certain commercially available catalysts, thereby demonstrating that the catalyst of the present disclosure can selectively and efficiently convert dissolved plastic in HVGO into light olefins.

According to a first aspect, the present disclosure relates to a zeolite catalyst.

More particularly, the catalyst comprises: an ultra-stable Y zeolite; and, a ZSM-5 zeolite. The ultra-stable Y-type zeolite is the main active component of the catalyst. In an embodiment, the catalyst comprises, based on the total weight of the catalyst from about 80 to about 95 wt. %, for example from about 80 to about 90 wt. % of the ultra-stable Y zeolite; and, from about 5 to about 20 wt. %, for example from about 10 to about 20 wt. % of the ZSM-5 zeolite.

ZSM-5 type zeolites have a high ratio of silicon to aluminum. In exemplary embodiments, the silica to alumina ratio by weight is from about 40:1 to about 80:1, for example from about 45:1 to about 75:1, or from about 50:1 to about 75:1. In one embodiment, the silica to alumina ratio by weight in the ZSM-5 zeolite is about 50:1. In another embodiment, the silica to alumina ratio by weight in the ZSM-5 zeolite is about 75:1.

Without intention to limit the present disclosure, the ultra-stable Y zeolite and the ZSM-5 zeolite are admixed in the aforementioned ratios by weight to form the catalyst. Conventionally, such admixing comprises the dry mixing of at least a fraction—and typically at least 90 wt. %, at least 95 wt. % or at least 99 wt. %—of the solid zeolites in an appropriate mixer. In certain embodiments, the zeolites are mixed using high intensity mixing—providing a mixing energy of at least 0.5 KW per 100 kg of ingredients—to ensure that a homogeneous mixture is obtained. The use of a flat-bladed mixer may also be of benefit.

Subject to the aforementioned ratios by weight within the catalyst, the ultra-stable Y-zeolite and the ZSM-5 zeolite may each, independently of one another, be a fresh or as-synthesized zeolite, a regenerated zeolite or a mixture thereof. Where applicable, regeneration of the or each zeolite catalyst may be effected by removing coke deposited in the pores thereof under heating in an oxygen atmosphere. Exemplary regenerative heating temperatures are from about 400 to about 800° C. or from about 500 to about 800° C.

In an embodiment, at least a fraction of the ZSM-5 zeolite in the catalyst is in its fresh or as-synthesized form. For example, at least 90 wt. %, at least 95 wt. % or at least 99 wt. % of the total amount of ZSM-5 zeolite in the catalyst is in its fresh or as-synthesized form.

There is no particular intention to limit the methods by which the ZSM-5 zeolite is synthesized. Exemplary methods of synthesis include those described in: EP Publication No. 0,068,817 A; U.S. Pat. Nos. 6,004,527; 4,522,705; EP Publication No. 0,156,595 A; U.S. Pat. No. 5,145,659; and, U.S. Pat. No. 6,261,534, the disclosures of which documents are incorporated herein by reference in their entirety. Moreover, the present disclosure envisages the synthesis of the ZSM-5 catalysts via either a method of organic templating or via a template-free method.

In certain preferred embodiments, the ZSM-5 zeolite of the catalyst is prepared by a hydrothermal synthesis method using an organic templating agent. More particularly, it is preferred that the ZSM-5 zeolite of the catalyst is prepared by a rapid ageing hydrothermal synthesis method using an organic templating method.

In the following exemplary rapid ageing hydrothermal synthesis of ZSM-5 zeolites, the organic templating agent serves the roles of structure-directing, space-filling, and charge-balancing during the zeolite crystallization. A solution of an aluminium salt is dissolved in an aqueous solution of the organic templating agent at a temperature of from about 10 to about 30° C.: the obtained mixture is stirred so to ensure homogeneity. In certain embodiments, the aluminium salt is selected from the group consisting of aluminium sulfate ($Al_2(SO_4)_3$), aluminium nitrate ($Al(NO_3)_3$), aluminium chloride ($AlCl_3$) and aluminium acetate ($Al(CH_3COO)_3$). A preference may be noted for the use of aluminium sulfate ($Al_2(SO_4)_3$). Further, exemplary templating agents, which may be used alone or in combination, include: tetrapropylammonium hydroxide (TPAOH); tetrapropylammonium bromide (TPABr); 6-hexanediol; 1,6-hexanediamine; 1-propanol; 1-propylamine; pentaerythritol; cetyltrimethylammonium (CTA) hydroxide; L-carnitine; and, L-lysine. It is preferred that the templating agent is either tetrapropylammonium hydroxide (TPAOH) or tetrapropylammonium bromide (TPABr): a particular preference for tetrapropylammonium hydroxide (TPAOH) may be mentioned.

Thereafter, at least one silicate ester is added to the aqueous mixture under stirring of the resulting gel and whilst elevating the temperature of the gel to from about 35 to about 90° C., for example to from about 35 to about 80° C. or from about 35 to about 70° C. In an embodiment, the at least one silicate ester is added slowly to the aqueous mixture and, more particularly, may be added in a dropwise manner to the aqueous mixture. At the elevated temperature, it is expected that the crystal growth rate will increase versus the nucleation rate. The gel may be stirred for a duration of from about 1 to about 20 hours to further reduce the nucleation rate.

The total amount of the at least one silicate ester added to the aqueous mixture will be determined by the descried Si/Al ratio of the ZSM-5 zeolite. In certain embodiments, the at least one silicate ester has the formula $R_{(4-x)}Si(OR^1)_x$, wherein R and $R^1$ are each independently $C_1$-$C_8$ alkyl and x is an integer of from 1 to 4. Exemplary silicate esters having utility in the method either alone or in combination include, but are not limited to: tetramethyl orthosilicate ($Si(OCH_3)_4$); methyltriethoxy orthosilicate ($Si(CH_3)(OC_2H_5)_3$); and, tetraethyl orthosilicate ($Si(OC_2H_5)_4$). In a preferred embodiment, aqueous solution includes tetraethyl orthosilicate ($Si(OC_2H_5)_4$).

The prepared gel is then subjected to hydrothermal heating. In some embodiments, the gel is hydrothermally heated at a temperature ranging from about 120° C. to about 240° C., for example from about 140° C. to about 220° C. or from about 160° C. to about 200° C. In some embodiments, the gel is hydrothermally heated at the aforementioned temperatures for a duration of from about 10 hours to about 48 hours, for example from about 12 hours to about 24 hours or from about 16 to about 24 hours. In an exemplary embodiment, the gel is hydrothermally heated at about 180° C. for about 18 hours.

The ZSM-5 zeolite formed in the hydrothermal treatment step is conventionally washed using deionized water and then dried at from about 70° C. to about 90° C. The templating agent of the ZSM-5 zeolite is then removed by calcination, conventionally at a temperature of from about 500° C. to about 800° C. or about 500° C. to about 700° C. Exemplary durations of this calcination step may be from about 2 to about 8 hours or from about 4 to about 8 hours. The calcination serves to burn-off the organic templating agent, yielding carbon dioxide therefrom, and thereby leaving voids which provide the pores or channels of the ZSM-5 zeolite.

Having regard to the ZSM-5 catalysts of the present matter, whenever an $Al^{3+}$ cation replaces a $Si^{4+}$ cation, an additional positive charge is required to keep the material charge-neutral. With a proton ($H^+$) as the cation, the material becomes very acidic. Thus, the acidity is proportional to the Al content. Herein, an ammonia temperature-programmed desorption ($NH_3$-TPD) method is used to measure the acidity of the ZSM-5 zeolite. In one embodiment, the ZSM-5 zeolite has a total acidity of from about 0.25 to about 0.75 mmol/g, for example from about 0.27 to about 0.72 mmol/g, from about 0.028 to 0.7 mmol/g, or from about 0.294 to about 0.686 mmol/g, as defined by $NH_3$-TPD. In one embodiment, the total acidity of the ZSM-5 zeolite is about 0.294 mmol/g. In another embodiment, the total acidity of the ZSM-5 zeolite is about 0.686 mmol/g. In yet another embodiment, the total acidity of the ZSM-5 zeolite is about 0.555 mmol/g.

In some embodiments, the ZSM-5 zeolite has a surface area, as determined by Brunauer-Emmett-Teller (BET) analysis, of from about 300 to about 400 m²/g, preferably from about 315 to about 350 m²/g: this surface area is much higher than commercially available zeolite (138 m²/g). In one specific embodiment, the ZSM-5 zeolite has a surface area of 316 m²/g. In another embodiment, the ZSM-5 zeolite has a surface area of 341 m²/g. In yet another embodiment, the ZSM-5 zeolite has a surface area of 349 m²/g. The BET hypothesis is the foundation for a significant analysis method for determining the specific surface area of a material. It attempts to explain the physical adsorption of gas molecules on a solid surface. Specific surface area is a property of solids, the total surface area of a material per unit of mass, solid or bulk volume, or cross-sectional area.

In one embodiment, the high surface area of the ZSM-5 zeolite may be attributed to the presence of both mesopores and micropores.

The mesopore surface area of the ZSM-5 zeolite is from about 150 to about 250 m²/g, for example from about 160 to about 240 m²/g, from about 170 to about 230 m²/g, from about 180 to about 225 m²/g, or from about 190 to about 225 m²/g, as determined by Barrett-Joyner-Halenda (BJH) desorption analysis. In an embodiment, the mesopore surface area of the ZSM-5 zeolite, as determined by BJH desorption analysis is from about 175 to about 250 m²/g. In one embodiment, the mesopore surface area of the ZSM-5 zeolite is about 190 m²/g. In another embodiment, the mesopore surface area of the ZSM-5 zeolite is about 213 m²/g. In yet another embodiment, the mesopore surface area of the ZSM-5 zeolite is about 225 m²/g.

In an embodiment, the micropore surface area of the ZSM-5 zeolite, as determined by Barrett-Joyner-Halenda (BJH) desorption analysis, is in the range of from about 11 to 140 m²/g, for example about 30 to about 140 m²/g, from about 50 to about 140 m²/g, from about 70 to about 140 m²/g, from about 90 to about 140 m²/g or from about 110 to about 140 m²/g. In one embodiment, the micropore surface area of the ZSM-5 zeolite is about 116 m²/g. In another embodiment, the micropore surface area of the ZSM-5 zeolite is about 126 m²/g. In yet another embodiment, the micropore surface area of the ZSM-5 zeolite is about 136 m²/g.

The mesopore volume of the ZSM-5 zeolite may be from about 0.070 to about 0.200 cm³/g, for example from about 0.08 to about 0.2 cm³/g, or from about 0.075 to about 0.200 cm³/g, as determined by BJH desorption analysis. In one embodiment, the mesopore volume of the ZSM-5 zeolite is about 0.080 cm³/g. In another embodiment, the mesopore volume of the ZSM-5 zeolite is about 0.18 cm³/g. In yet another embodiment, the mesopore volume of the ZSM-5 zeolite is about 0.11 cm³/g.

In an embodiment, the ZSM-5 zeolite has a median pore diameter of from about 2 to about 6 nm, as determined by BJH desorption analysis.

In some embodiments, the catalyst disclosed herein can be used in combination with metal promoters including, but not limited to, platinum, palladium, ruthenium, rhenium, cobalt, molybdenum, nickel, iron, manganese, another metal, or a combination thereof.

The catalyst of the present disclosure can be used for converting a solution of low density polyethylene (LDPE) in heavy vacuum gas oil (HVGO) to produce $C_2$-$C_4$ olefins via a fluid catalytic cracking (FCC) process, as described in FIG. 1A. Although the description herein provided refers to conversion of LDPE (used in plastics) to light olefins, in one embodiment, the method of the present disclosure can be adapted to convert high-density polyethylene (HDPE), polypropylene (PP), polystyrene (PS), polyethylene terephthalate (PET), polyurethanes (PU), or a combination thereof as well, albeit with a few variations, as may be obvious to a person skilled in the art. The order in which the process 50 is described is not intended to be construed as a limitation, and any number of the described method steps may be combined to implement the process 50. Additionally, individual steps may be removed or skipped from the process 50 without departing from the spirit and scope of the present disclosure.

The FCC apparatus which may be used in the present disclosure will conventionally have a regeneration zone (a regenerator), a reaction zone (a reactor), a separation zone (a separator), and a stripping zone (a stripper). The term "fluid catalytic cracking" referred to herein indicates that the solution of LDPE in HVGO, is continuously brought into contact with a catalyst which is kept in a fluidized state under specific operating conditions, to crack the heavy-fraction oil, thereby producing light-fraction hydrocarbons, mainly comprising gasoline and light-fraction olefins ($C_2$ to $C_4$).

At step 52, the process 50 includes fluidizing a stream of the solution of the LDPE in the HVGO in a riser reactor. Initially, LDPE is dissolved in HVGO to obtain a homogeneous solution, prior to the fluidization process. HVGO acts as a solvent and carrier for LDPE. In some embodiments, other solvents, preferably heavy-fraction oils known in the art, may be used singly or jointly, or as a mixture thereof, with a minor portion of a light fraction oil.

In some embodiments, the solution of the LDPE in the HVGO includes about 1 to about 15 wt. %, preferably from about 2 to about 15 wt. %, of the LDPE, based on the total weight of the solution. In some embodiments, the solution may have: a carbon content of from about 85 to about 90 wt. %; and, a hydrogen content of from about 10 to about 15 wt. %, based on the weight of the solution. In some embodiments, the solution may have: a sulfur content of from about 4000 to about 6000 parts per million by weight; and, a nitrogen content of from about 150 to about 250 parts per millions by weight. In some embodiments, the solution of the LDPE in the HVGO has a density of from about 0.85 to about 0.95 g/cm³, preferably from about 0.87 to about 0.93 g/cm³ or from about 0.89 to about 0.91 g/cm³.

The fluidization process takes place in the reactor, of which a preferred form is a riser reactor; in some embodiments, a downer reactor may alternatively be used. The solution of the LDPE in the HVGO is fed into the riser reactor to crack the LDPE in HVGO, thereby producing light-fraction hydrocarbons, mainly including olefins. Typically steam, nitrogen, or hydrocarbon vapors are used to aid atomization and fluidization of the LDPE-HVGO solution. One of the critical parameters that affects the fluidization of the solution is weight hourly space velocity. In an embodiment, the stream of the solution of the LDPE in HVGO is fed into the riser reactor at a weight hourly space velocity of from about 1 to about 20 hr⁻¹, for example from about 2 to about 20 hr⁻¹, from about 5 to about 20 hr⁻¹ or from about 5 to about 15 hr⁻¹.

At step 54, the process includes cracking the solution stream with the catalyst in the riser reactor to produce a cracked stream and spent catalyst. In this step, the solution stream of LDPE in HVGO is continuously bought in contact with the catalyst under specific operating conditions, to crack the LDPE in HVGO.

In some embodiments, the ratio by weight of the catalyst to the solution is from about 3:1 to about 9:1, for example from about 3:1 to about 8:1, from about 4:1 to about 8:1, from about 4:1 to about 7:1 or from about 4:1 to about 6:1. In a preferred embodiment, the ratio by weight of the catalyst to the solution is about 5:1.

The cracking of the solution stream generally takes place at high temperatures and with a short contact time. In an embodiment, the fluid catalytic cracking is performed at a temperature of from about 500 to about 700° C., preferably 525 to about 650° C., and more preferably from about 525 to about 575° C. Although the FCC process can be performed at higher temperatures, it is preferred that the FCC process is performed at a temperature of about 550° C.

The cracking process results in the formation of the cracked steam and the spent catalyst. The cracked steam comprises at least one $C_2$-$C_4$ olefin. Such olefins are included in the product stream within a mixture of hydrocarbons of which exemplary constituents include but are not limited to: dry gas ($H_2$, $C_1$-$C_2$); ethylene; propylene; light olefins ($C_{2=}$-$C_{4=}$); total gas ($H_2$, $C_1$-$C_4$); naphtha ($C_5$-$C_{10}$); light cycle oil (LCO) ($C_{10}$-$C_{14}$); heavy cycle oil (HCO) ($C_{14}$-$C_{40}$); and, coke.

At step 56, the process includes separating the cracked stream and the spent catalyst in a separator. The cracked steam is separated from the catalyst in the separator where most of the hydrocarbons are separated from the spent catalyst. The spent catalyst may, in certain embodiments, be further sent to a stripper, where any fraction of the residual hydrocarbons—which may comprise both products and unreacted materials—which are adsorbed onto the catalysts, are removed from the catalyst particles. The catalyst is conventionally further sent to a regenerator, where it is burned off with air to restore catalytic activity before being recirculated into the reactor.

EXAMPLES

The following examples demonstrate a process for producing C2-C4 olefins by fluid catalytic cracking of a solution of low-density polyethylene (LDPE) in heavy vacuum gas oil in the presence of a zeolite catalyst. The examples are provided solely for illustration and are not to be construed as limitations of the present disclosure, as many variations thereof are possible without departing from the spirit and scope of the present disclosure.

The following commercially available product was used in the Examples:
  E-cat: Ultra-stable Y zeolite sourced from a refinery in The Kingdom of Saudi Arabia.
  ZSM-5(COM): Commercially available ZSM-5 zeolite sourced in The Kingdom of Saudi Arabia.

Example 1: Synthesis of ZSM-5 Zeolites

Mesoporous ZSM-5 additives were synthesized using a hydrothermal rapid aging synthesis approach. The rapid aging synthesis approach at high temperatures is employed to tune the zeolite's textural properties and crystal size, which are often beneficial for shape-selective catalysis [See: Hernández-Giménez, A. M., Heracleous, E., Pachatouridou, E., Horvat, A., Hernando, H., Serrano, D. P., Lappas, A. A., Bruijnincx, P. C. A., Weckhuysen, B. M., (2021), "*Effect of Mesoporosity, Acidity and Crystal Size of Zeolite ZSM-5 on Catalytic Performance during the Ex-situ Catalytic Fast Pyrolysis of Biomass*", Chem. Cat. Chem. 13, 1207-1219, the disclosure of which is incorporated herein by reference in its entirety]. 0.1694 g of $Al_2(SO_4)_3 \cdot xH_2O$ was dissolved in a solution containing 2.5 ml tetrapropylammonium hydroxide (TPAOH, 40% solution in water) and 53 ml deionized water. The TPAOH is used as the template, playing the role of structure-directing, space-filling, and charge-balancing during the zeolite crystallization. The obtained solution was stirred for 1 hour using a magnetic stirrer at 600 rpm to ensure homogeneity. Thereafter, 11.2 ml of tetraethyl orthosilicate (reagent grade, 98%) was added slowly into the solution mixture, the stirring rate was increased to 700 rpm, and the solution temperature was raised to 40° C. At this temperature, crystal growth rate increased relative to the nucleation rate. The solution was stirred for 1.5 hours to shorten the nucleation rate before transferring the solution into a Teflon-lined autoclave, which autoclave was inserted into an oven at 180° C. for 15 hours. The resultant ZSM-5 zeolite—having a Si/Al ratio of 50 (ZSM-5(50)) was washed three times with deionized water and dried in an oven at 90° C. before removing the template by calcination under the flow of air in a muffle furnace at 600° C. for 6 hours. During the calcination, the template is burnt into carbon dioxide, thus leaving a void space that forms the pores or channels of the zeolite.

ZSM-5(25) and ZSM-5(75) were synthesized using the same approach. By varying the Si/Al ratio, the ZSM-5 acidity was varied since it plays a significant role in catalytic activity ([See: Umar, M., Abdulazeez, I., Tanimu, A., Ganiyu, S. A., Alhooshani, K., (2021), *"Modification of ZSM-5 mesoporosity and application as catalyst support in hydrodesulfurization of dibenzothiophene: Experimental and DFT studies", J. Environ. Chem. Eng.*, 9., 106738, the disclosure of which is incorporated herein by reference in its entirety]).

Example 2: Characterization of Synthesized ZSM-5 Zeolites

The crystallinities of the ZSM-5 additives with Si/Al ratios of 25, 50, and 75, respectively, and the ZSM-5(COM) were independently measured by X-ray diffraction technique using a Rigaku Miniflex II benchtop diffractometer. The analysis was performed using Cu Kα as the X-ray radiation source operating at a voltage of 30 kV, a current of 15 mA, and a scan rate of 3°/min, covering the 2θ range of from 5 to 60°.

The zeolite acidity and acid strengths were determined using the temperature-programmed desorption of ammonia technique using a BELCAT unit. The analysis involves drying 0.1 g of zeolite sample at 100° C. for 1 hour and subsequently ramping the temperature thereof to 500° C.: the zeolite sample is then maintained at 500° C. for 1 hour under a continuous flow of helium (He) gas. Thereafter, the sample was cooled down before purging a 95/5 vol. % of He/NH$_3$ into the sample for 30 minutes. Later, the excess He/NH$_3$ gas mixture was itself purged out under continuous a flow of He gas for 10 minutes. The desorption of adsorbed NH$_3$ was recorded at a temperature ramping of 10° C./min until a temperature 550° C. was attained.

The surface area and porosity of the zeolites were measured using nitrogen adsorption-desorption isotherms and analyzed at 77 K using Micromeretics ASAP 2020.

The morphology of the zeolites was evaluated using high-resolution Field emission scanning electron microscopy (FE-SEM).

Example 3: Catalytic Cracking Reaction

The catalytic cracking reaction of HVGO and LDPE/HVGO blends was conducted in a fixed-bed microactivity test (MAT) unit according to ASTM Standard Method D3907. Before the cracking reaction, the synthesized ZSM-5 and ZSM-5(COM) additives were mixed with E-Cat to form a catalyst composition with 15% ZSM-5 in E-Cat, then steam deactivated for 6 hours at 810° C. under a flow of air and a steam rate of 3 cm$^3$/minute. The catalyst (5 g) was loaded into a stainless-steel tubular reactor—having an internal diameter of 22 mm and a length of 38 cm—and was held in position using quartz wool before and after the loading. The reactor was placed in the furnace, and preheaters, a nitrogen gas line, and a feed injector were clamped to the reactor. After the reaction, gaseous products from the reaction and stripping modes were collected in a gas burette by water displacement. The weight of the feed syringe was determined before and after the experiment to obtain the exact weight of the oil fed.

After completion of the cracking reaction, the obtained products—including gaseous, and liquid products, and coke—were analyzed. For the analysis of gaseous products, Agilent 3000A Micro GC, linked with four thermal conductivity detectors (TCD), was used. The detector enables quantitative determination of all light hydrocarbons from C1 to C5, as well as hydrogen gas using the Refinery Gas Analysis (RGA) standard method. For the liquid products analysis, simulated distillation was carried out using a Shimadzu GC 2010Plus lined with a flame ionization detector (FID). The deposited coke on the used catalyst was oxidized via air regeneration, and the produced CO$_2$ was measured using the 1440 Infra-Red Gas Analyzer, and carbon content was determined.

The feed conversion was calculated as follows:

$$\% \text{ Conversion} = (100 - \text{LCO (wt. \%)} - \text{HCO (wt. \%)} \text{ for HVGO and HVGO blends, where LCO (wt. \%)} = \text{Light cycle oil (wt. \%) and HCO} = \text{Heavy cycle oil (wt. \%).}$$

An experimental mass balance, x, of 96%<x<102% validates each of the MAT runs.

Results and Discussion

Figures 2A, 2B:
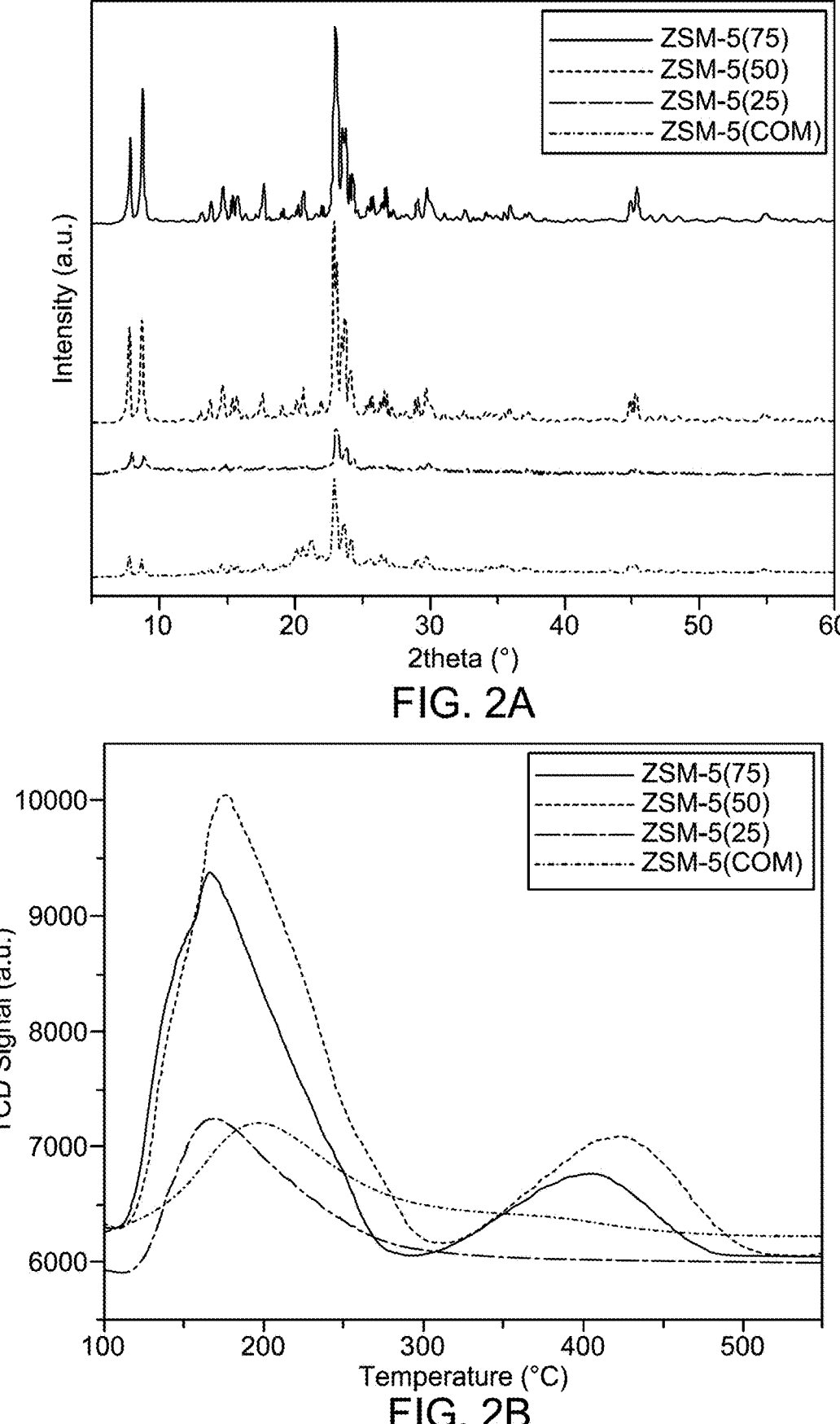
FIG. 2A shows X-ray diffractogram pattern of ZSM-5 and commercial ZSM-5 additive (ZSM-COM) zeolites, according to certain embodiments.
FIG. 2B shows ammonia temperature programmed desorption ($NH_3$-TPD) profiles of ZSM-5 and ZSM-COM zeolites, according to certain embodiments.

Characterization of synthesized ZSM-5 and ZSM-5 (COM) zeolites: FIG. 2A presents the crystal structure of all the zeolite additives exhibiting Mobil-Five (MFI) structure, with major diffraction peaks at 8°, 15°, 23,° and 45° [See: Jermy, B. R., Tanimu, A., Siddiqui, M. A., Qureshi, Z. S., Aitani, A., Akah, A., Xu, Q., AlHerz, M., (2023), *"Crude oil conversion to chemicals over green synthesized ZSM-5 zeolite", Fuel Processing Technology* 241, 107610, the disclosure of which is incorporated herein by reference in its entirety]. The MFI-type zeolites are characterized by two interconnected channel systems containing pentasyl units and are often regarded as medium pore-size zeolites [See: Shamzhy, M., Gil, B., Opanasenko, M., Roth, W. J., Čejka, J., (2021), *"MWW and MFI frameworks as model layered zeolites: Structures, transformations, properties, and activity. ACS Catal.* 11, 2366-2396, the disclosure of which is incorporated herein by reference in its entirety]. It is noted that the degree of crystallization and crystal growth were different in all the zeolites. The ZSM-5(COM) and ZSM-5 (25) have relatively lower peak intensity than the ZSM-5 (50) and ZSM-5(75), which may imply the formation of small crystal sizes. In addition, because the peaks of ZSM-5(25) were not well resolved, it may also imply that the fast aging at high temperatures during the zeolite synthesis affects the complete crystallization process. However, the peaks of ZSM-5(50) and ZSM-5(75) have high intensities, and this implies the formation of a relatively large crystal size; the observed peaks are very well resolved, signifying complete crystallization.

The $NH_3$-TPD profiles of ZSM-5(COM) and the synthesized ZSM-5 zeolites are shown in FIG. 2B. The ZSM-5 (COM) shows two broad peaks; the first peak appears between 10° and 250° C., which is attributed to weak acid sites, and the second peak between 25° and 400° C. is attributed to the moderate acid sites. Similarly, ZSM-5(25) zeolite has two broad peaks; the first peak is attributed to weak acid sites. However, the second peak appears at a desorption temperature greater than 400° C. and is ascribed to strong acid sites. Based on the desorption profiles, the ZSM-5(COM) does not have strong acid sites, while ZSM-5(25) does not have moderate acid sites. ZSM-5(50) and ZSM-5(75) profiles have all three acid sites, although in different proportions. Table 1 summarizes the amount of acid sites and total acidity for all the ZSM-5 additives.

TABLE 1

Acidity parameters of the zeolite additives.

| Zeolite | 100-250° C. (mmol/g) | 250-400° C. mmol/g) | >400° C. (mmol/g) | Total acidity (mmol/g) |
|---|---|---|---|---|
| ZSM-5(COM) | 0.283 | 0.051 | | 0.334 |
| ZSM-5(25) | 0.154 | — | 0.140 | 0.294 |
| ZSM-5(50) | 0.440 | 0.170 | 0.076 | 0.686 |
| ZSM-5(75) | 0.350 | 0.098 | 0.107 | 0.555 |

The ZSM-5(COM) has weak acid sites of 0.283 mmol/g and moderate acid sites of 0.051 mmol/g, while the ZSM-5(25) zeolite has large strong acid sites of 0.140 mmol/g and small weak acid sites of 0.154 mmol/g, making a total acidity of 0.294 mmol/g. The ZSM-5(50) has a large amount of weak acid sites of 0.440 mmol/g, medium acid sites of 0.170 mmol/g, and relatively small strong acid sites of 0.076 mmol/g: the total acidity of the ZSM-5(50) zeolite is 0.686 mmol/g. The ZSM-5(75) has 0.350 mmol/g of weak acid sites, 0.098 mmol/g of medium acid sites, and 0.107 mmol/g of strong acid sites: the total acidity of the ZSM-5(75) zeolite is 0.555 mmol/g.

As noted, ZSM-5(25) has the largest amount of strong acid sites but its total of acid sites is quite small compared to the other high silica zeolites. The most probable reason for this is that some of the aluminum species did not coordinate with the silica during the rapid aging synthesis, and thus the nucleation process was not completed. This may imply that the adopted synthesis approach is unfavorable for low Si/Al ratio zeolites such as ZSM-5(25). The ZSM-5(50) has a total acidity of 0.686 mmol/g, which is higher than the total acidity of ZSM-5(75). However, its strong acid sites are present in a smaller concentration than those available in ZSM-5(75). Strong acid sites are considered to be important for catalytic cracking reactions of bulky hydrocarbon molecules; however, bimolecular reactions such as hydride transfer will be intensified on the acid sites and thus will consume the formed light olefins [See: He, X., Tian, Y., Qiao, C., Liu, G., (2023), *Acid-driven architecture of hierarchical porous ZSM-5 with high acidic quantity and its catalytic cracking performance. Chemical Engineering Journal* 473, 145334, the disclosure of which is incorporated herein by reference in its entirety].

Figures 2C, 2D:
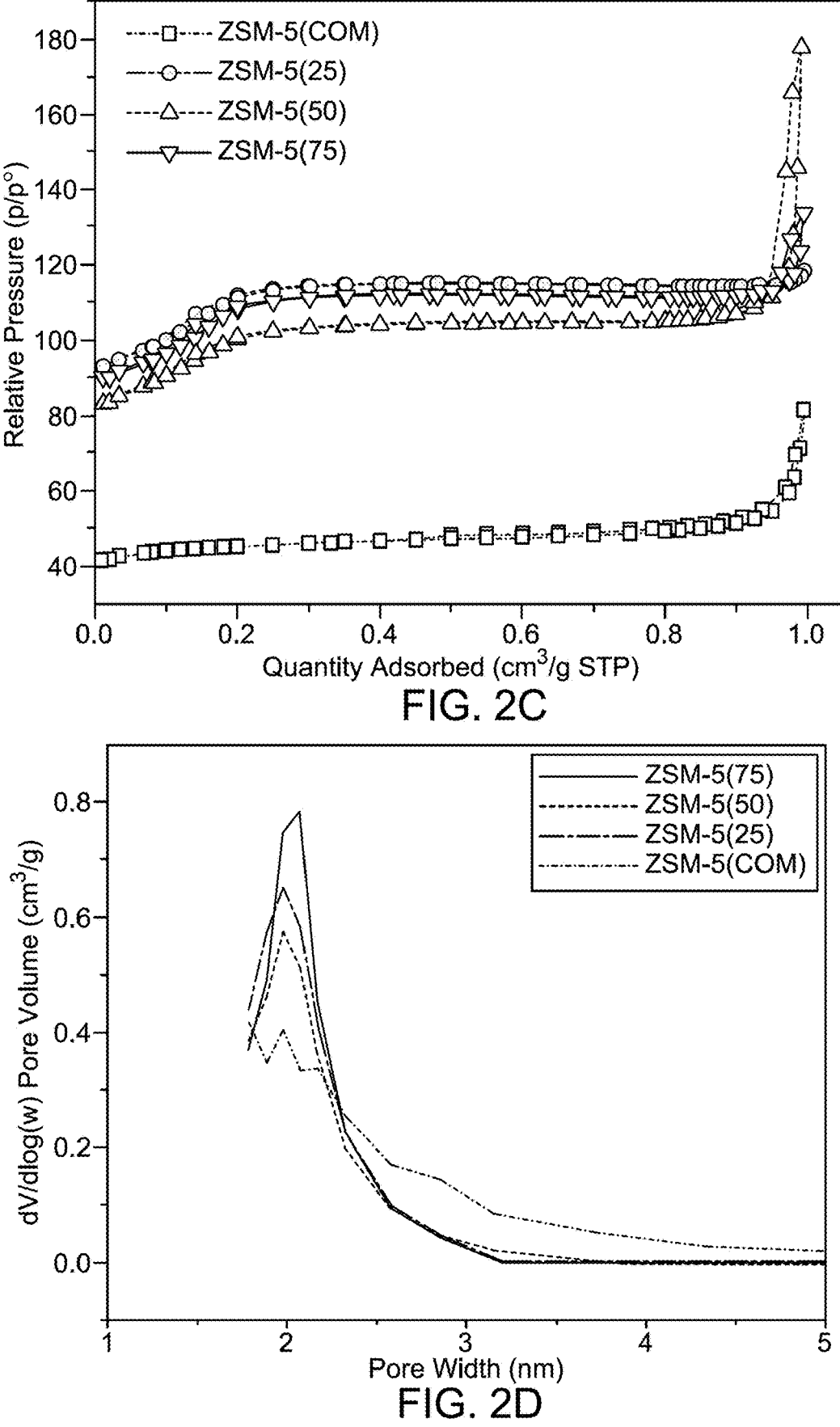
FIG. 2C shows a $N_2$ adsorption-desorption isotherm of ZSM-5 and ZSM-COM zeolites, according to certain embodiments.
FIG. 2D shows pore size distributions of ZSM-5 and ZSM-COM zeolites, according to certain embodiments.

The surface area and pore structure are other important parameters influencing catalyst activity and selectivity. As shown in FIG. 2C, all the ZSM-5 zeolites have a type IV hysteresis loop, as indicated by the adsorption-desorption isotherm profiles. This implies that the zeolites are mesoporous, as confirmed by their pore sizes (nm) in Table 2 herein below. However, the ZSM-5(COM) and ZSM-5(25) have a reasonable amount of microporosity, as noted in the micropore surface area and in the ratio of mesopore volume and micropore volume, as compared to the other zeolites. The pore size distribution plot is presented in FIG. 2D. ZSM-5(50) has the largest pore size (5.59 nm), although it has the lowest mesopore surface area (190 $m^2$/g). ZSM-5 (75) has the largest mesopore surface area and a moderate pore size of 2.98 nm.

The synthesized zeolites have a BET surface area in the range of 315-350 $m^2$/g, which is the typical BET surface area of ZSM-5 zeolite [See: Usman, A., Siddiqui, M. A. B., Hussain, A., Aitani, A., Al-Khattaf, S., (2017), "*Catalytic cracking of crude oil to light olefins and naphtha: Experimental and kinetic modeling*", *Chemical Engineering Research and Design* 120, 121-137, the disclosure of which is incorporated herein by reference], while the ZSM-5 (COM) has a BET surface area of 138 $m^2$/g and mesopore surface area of 26 $m^2$/g.

TABLE 2

| Surface area and porosity of the synthesized and commercial ZSM-5 zeolites Catalyst | BET surface area ($m^2$/g) | Mesopore surface area ($m^2$/g) | Micropore surface area ($m^2$/g) | Micropore volume ($cm^3$/g) | Mesopore volume ($cm^3$/g) | $V_{Meso}$/ $V_{Micro}$ | Pore size (nm) |
|---|---|---|---|---|---|---|---|
| ZSM-5 (COM) | 138 | 26 | 112 | 0.059 | 0.066 | 1.12 | 3.65 |
| ZSM-5 (25) | 349 | 213 | 136 | 0.077 | 0.080 | 1.03 | 2.22 |
| ZSM-5 (50) | 316 | 190 | 126 | 0.071 | 0.18 | 2.53 | 5.59 |
| ZSM-5 (75) | 341 | 225 | 116 | 0.067 | 0.11 | 1.64 | 2.98 |

Figure 3A:
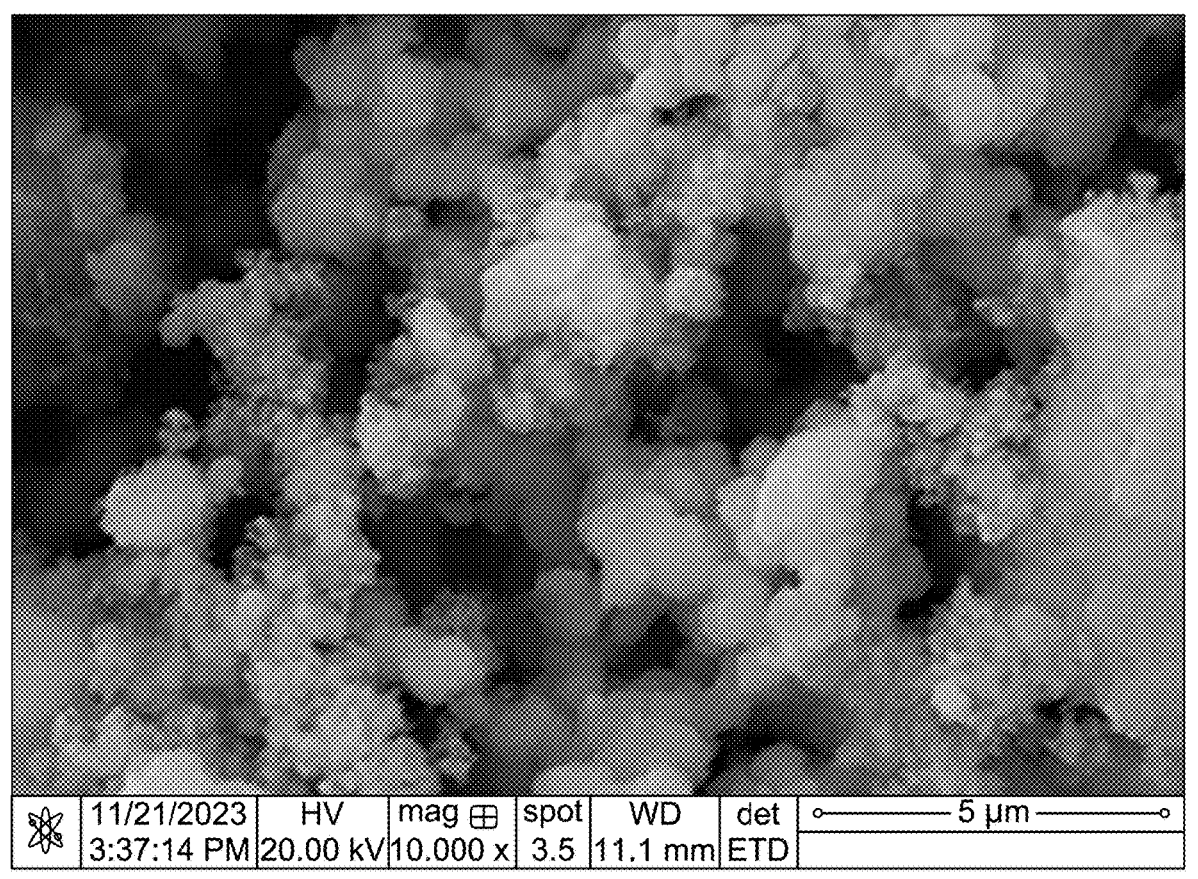
FIG. 3A shows a field emission scanning electron microscopy (FE-SEM) image of ZSM-5(25) at low magnification, according to certain embodiments.
Figure 3B:
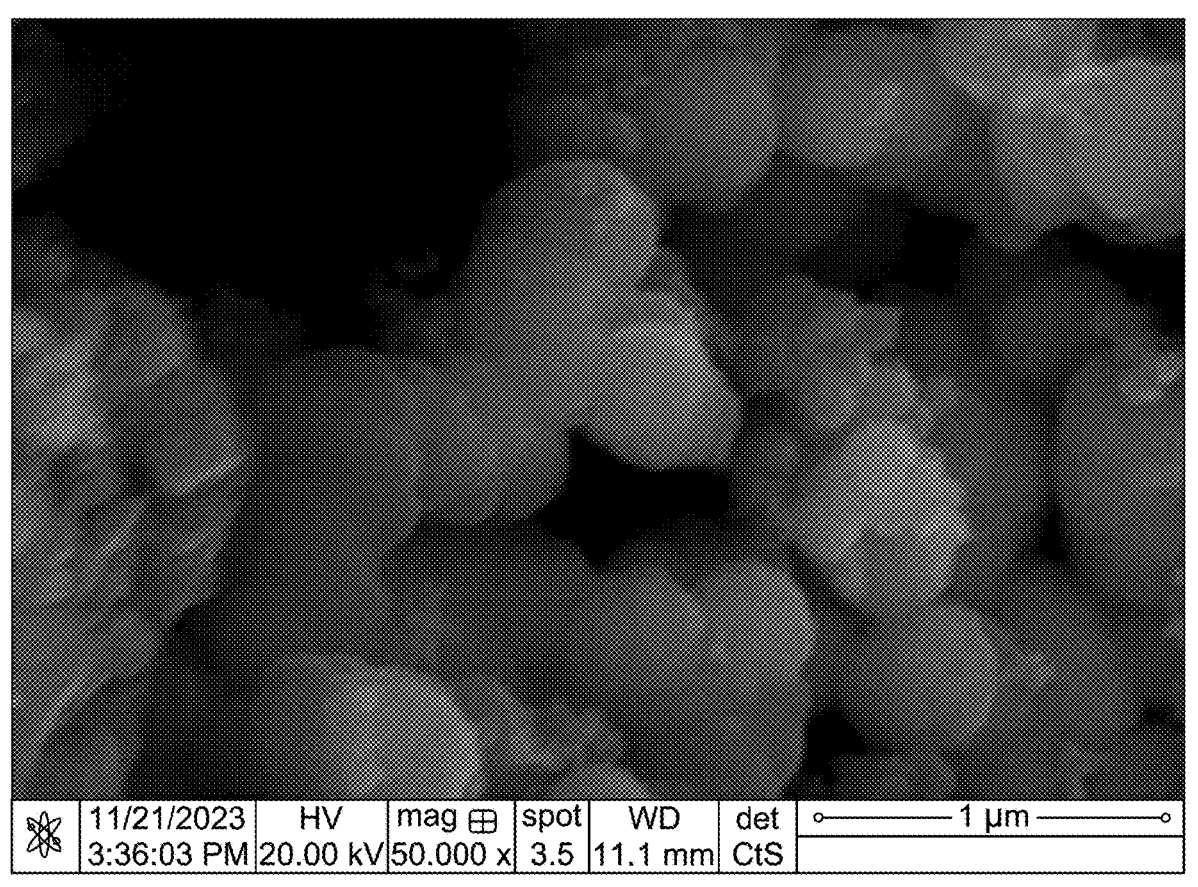
FIG. 3B shows a FESEM image of ZSM-5(25) at a magnification of 50000, according to certain embodiments.

FIG. 3A presents the morphology of the catalysts based on FE-SEM results in which ZSM-5(25) shows spherical-like morphology with particles of uniform sizes [See: Zhang, L., Jiang, Z. X., Yu, Y., Sun, C. S., Wang, Y. J., Wang, H. Y., (2015), "*Synthesis of core-shell ZSM-5@meso-SAPO-34 composite and its application in methanol to aromatics*", *RSC Adv.* 5, 55825-55831, the disclosure of which is incorporated herein by reference in its entirety]. The presence of nano-sized grains dispersed on the ZSM-5(25) surface indicates that the zeolite nucleation process is not complete, which is related to the relatively low intensity of the XRD diffraction peaks of the ZSM-5(25). The magnified morphology, as shown in FIG. 3B, indicates that ZSM-5(25) particle sizes are in the nanometer range.

Figure 3C:
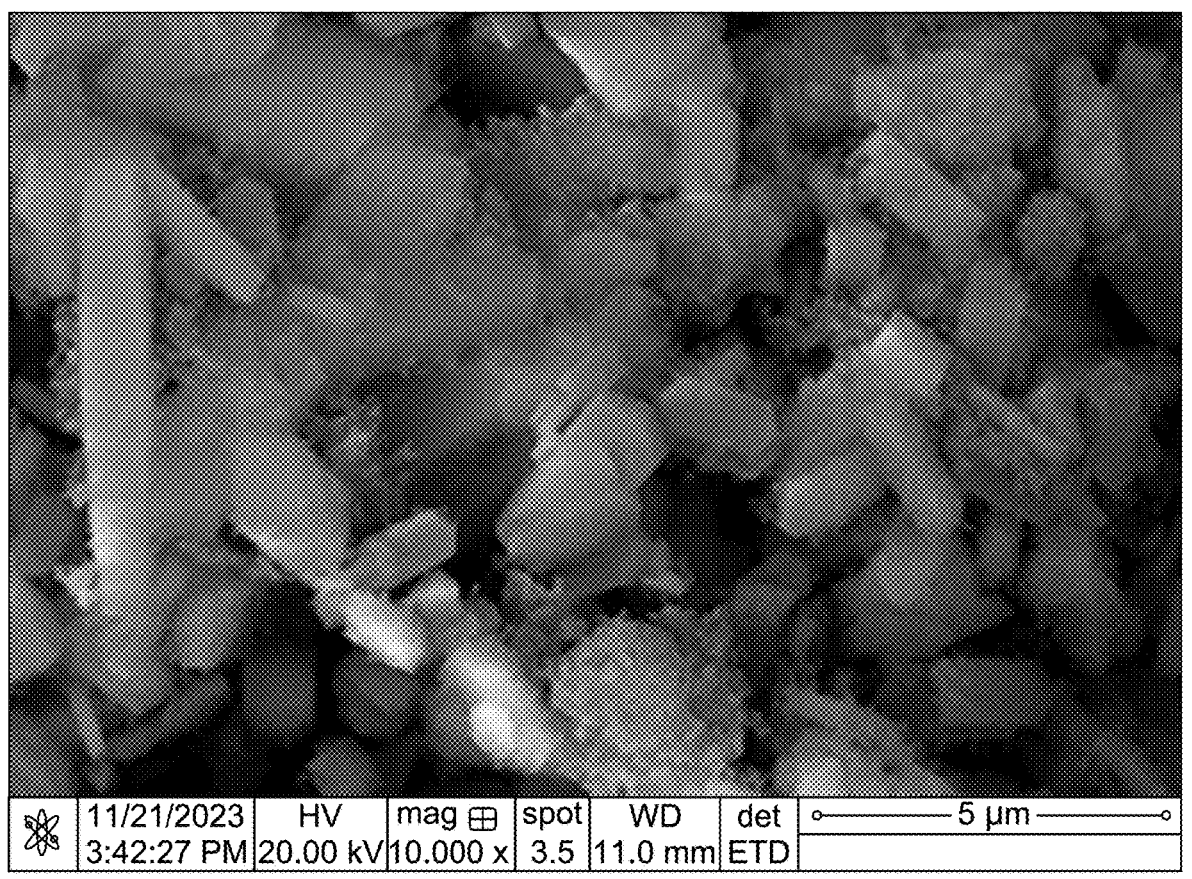
FIG. 3C shows a FESEM image of ZSM-5(50) at a magnification of 10000, according to certain embodiments.
Figure 3D:
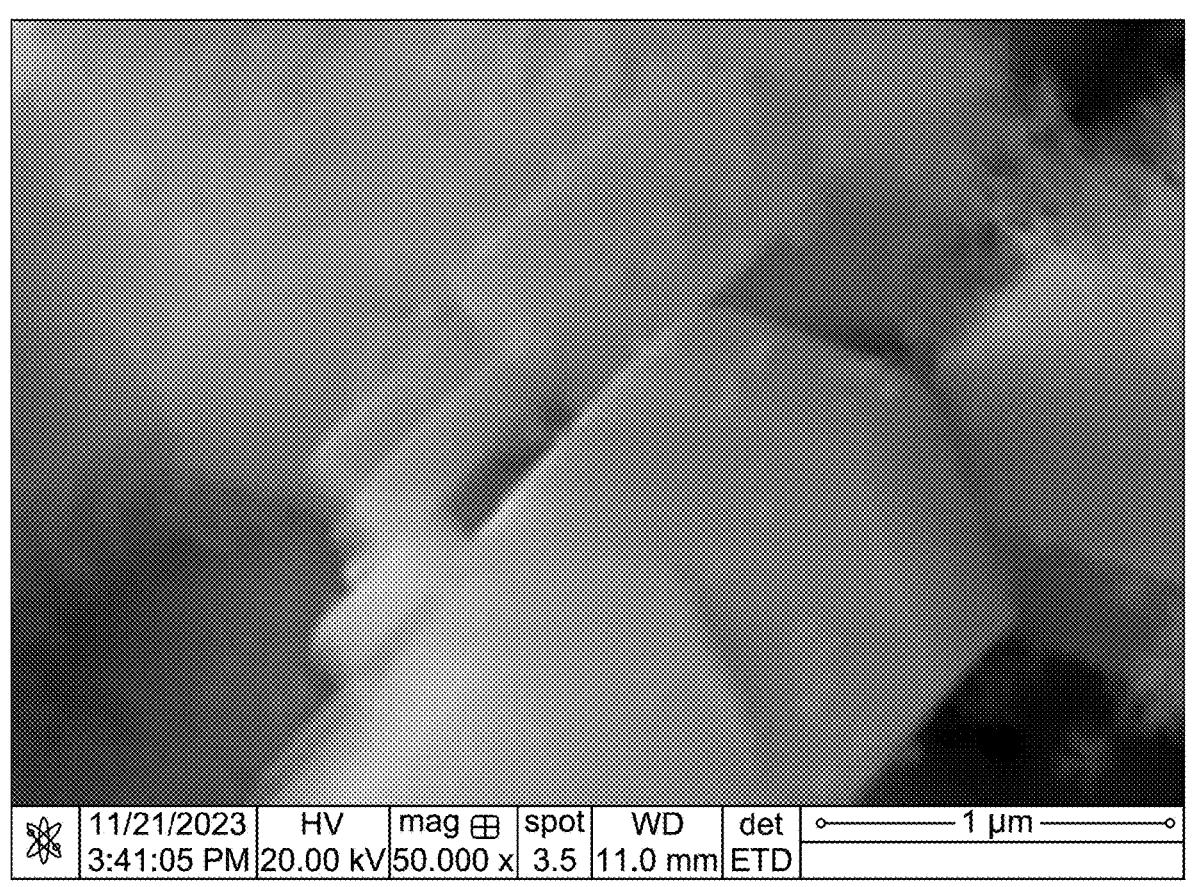
FIG. 3D shows a FESEM image of ZSM-5(50) at a magnification of 50000, according to certain embodiments.

The variation of the Si/Al ratio using the same rapid aging synthesis approach resulted in a gradual change in zeolite morphology. The ZSM-5(50) shows coffin-shaped particles in the micrometer range sizes as displayed in FIG. 3C. From the magnified morphology in FIG. 3D, it is noticed that the thickness of the ZSM-5(50) crystal (defined by the b-axis) is in the range of 100-200 nm, resulting in a short channel along the plate surface of the zeolite. This is reflected in the large mesopore volume and pore size of the ZSM-5(50) zeolite [See: Dai, W., Kouvatas, C., Tai, W., Wu, G., Guan, N., Li, L., Valtchev, V., (2021), *"Platelike MFI Crystals with Controlled Crystal Faces Aspect Ratio"*, J. Am. Chem. Soc. 143, 1993-2004, the disclosure of which is incorporated herein by reference in its entirety].

Figure 3E:
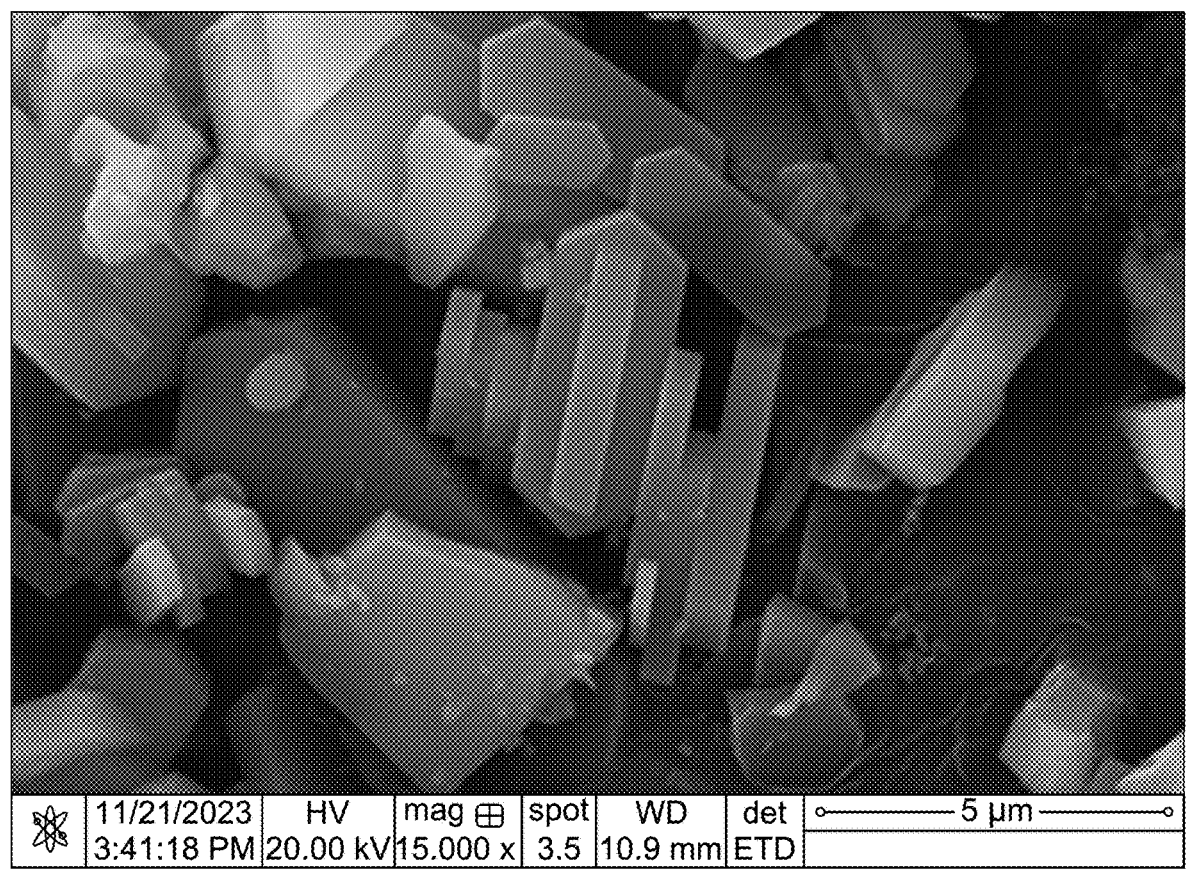
FIG. 3E shows a FESEM image of ZSM-5(75) at a magnification of 15000, according to certain embodiments.
Figure 3F:
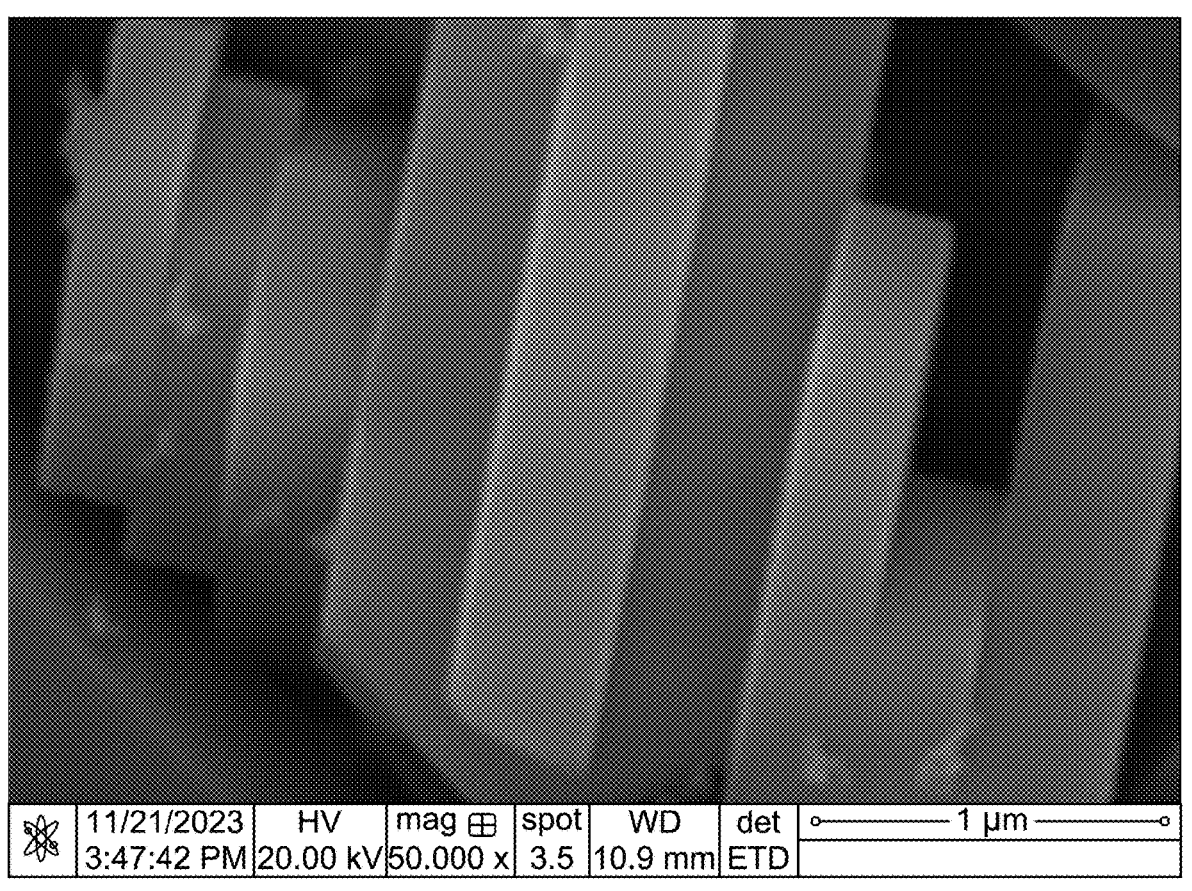
FIG. 3F shows a FESEM image of ZSM-5(75) at a magnification of 50000, according to certain embodiments.

The coffin-shaped morphology gradually transformed to twin intergrowth crystal morphology as the Si/Al increased to 75. FIG. 3E shows the morphology of ZSM-5(75) zeolite, which is a combination of coffin-shaped and 90° twin intergrowth of orthorhombic-shaped crystal particles, all in the micrometer ranges, as further shown in FIG. 3F. By analysis of magnified morphologies of the zeolites, it was observed that ZSM-5(75) has the largest crystal size while ZSM-5(25) has the smallest crystal size.

Figure 4:
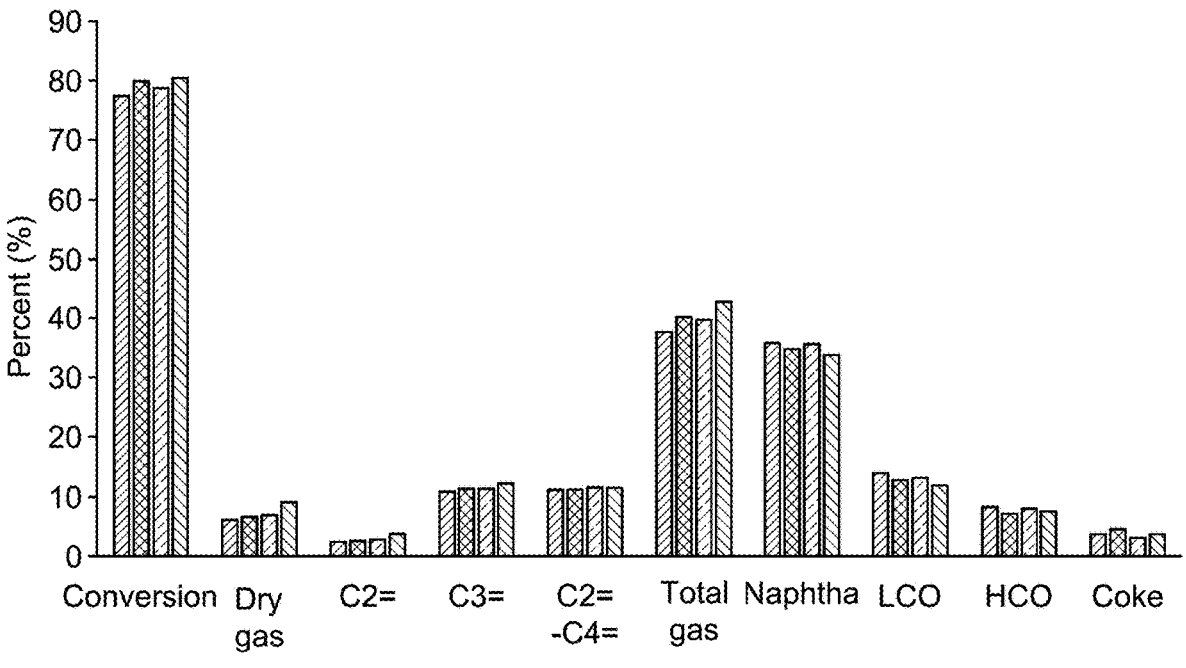
FIG. 4 shows micro-activity test results (conversion and yields) of the cracking of heavy vacuum gas oil (HVGO) and blends with low-density polyethylene (LDPE) over an equilibrium catalyst (E-Cat) at 600° C. and catalyst-to-oil ratio (C/O) of 5, according to certain embodiments.

Cracking over E-Cat: The effect of co-cracking LPDE with HVGO was studied by blending different amounts of LDPE in HVGO and charging about 1 g of the blended feed into the MAT reactor unit loaded with 5 g of E-Cat, resulting in a catalyst-to-oil (C/O) ratio of 5. The MAT reactor was set at 600° C. and a 30 second feed injection time was employed. FIG. 4 shows the performance comparison plot—conversion and product yields—for all the studied feedstocks. The products comprise dry gas ($H_2$, $C_1$-$C_2$), ethylene, propylene, light olefins ($C_{2=}$-$C_{4=}$), total gas ($H_2$, $C_1$-$C_4$), naphtha ($C_5$-$C_{10}$), LCO ($C_{10}$-$C_{14}$), HCO ($C_{14}$-$C_{40}$), and coke.

The HVGO conversion slightly increased with the blending of LDPE, although not proportionally. For example, an HVGO conversion of 77.5% was achieved, increasing to 80.4% in 10 wt. % LDPE/HVGO, wherein the stated wt. % is based on the total weight of the solution. However, the conversion of 5 wt. % LDPE/HVGO was slightly less than the conversion of 2.5 wt. % LDPE/HVGO. Although there are differences in the conversion for the various LDPE/HVGO blends, the absolute and relative differences in their conversion ratio are small. This observation may be related to the changes in the feed properties due to the dissolution of various weight percentages of the LDPE.

FIG. 4 also presents the effect of LDPE blending on the yields of total gas, naphtha, light cycle oil (LCO), and heavy cycle oil (HCO). The observed general trend is that adding LDPE increased total gas yield from 37.9% in HVGO feed to 42.8% in 10 wt. % LDPE/HVGO. This increase was associated with a corresponding increase in the dry gas and light olefins yields. Although the dry gas increased from 3.8% in HVGO to 5.4% in 10 wt. % LDPE/HVGO, the increase in total gas was largely due to the increase in light olefins, particularly ethylene and propylene. Therefore, it follows that the blending of LDPE with HVGO increased the yield of said light olefins under the stated conditions. This could be ascribed to the random scission cracking mechanism under the high-temperature condition that resulted in the decomposition of plastics to light olefins and some linear paraffin in addition to the bimolecular cracking mechanism that occurred on the acidic sites of the catalyst [See: Yan, G., Jing, X., Wen, H., Xiang, S., (2015) *"Thermal*

*cracking of virgin and waste plastics of PP and LDPE in a semi-batch reactor under atmospheric pressure"*, Energy and Fuels 29, 2289-2298, the disclosure of which is herein incorporated by reference]. The distribution of liquid products was also affected by the LDPE blending. The yield of naphtha, LCO, and HCO decreased proportionately with the increase in the LDPE percentage in the solution feed. Generally, adding LDPE is expected to increase the yield of light distillates—gas products and naphtha fraction—and lower the yield of LCO and HCO. This is due to the structure of LDPE, which is composed of short and long-chain branched olefins that can be cracked into small chains of olefins that oligomerize to form light distillates. However, the observed decrease in naphtha yield during cracking of LDPE/HVGO blends may imply that the formed naphtha fractions were further cracked into gaseous products. The decrease in LCO and HCO yield is attributed to the decrease in the heavy hydrocarbons often present in the HVGO feedstock due to the blending with LDPE. The percent of coke deposited on the catalysts did not show a clear trend for the distinct feedstocks: the coke yield (%) was within 3.78±0.5.

Figure 5A:
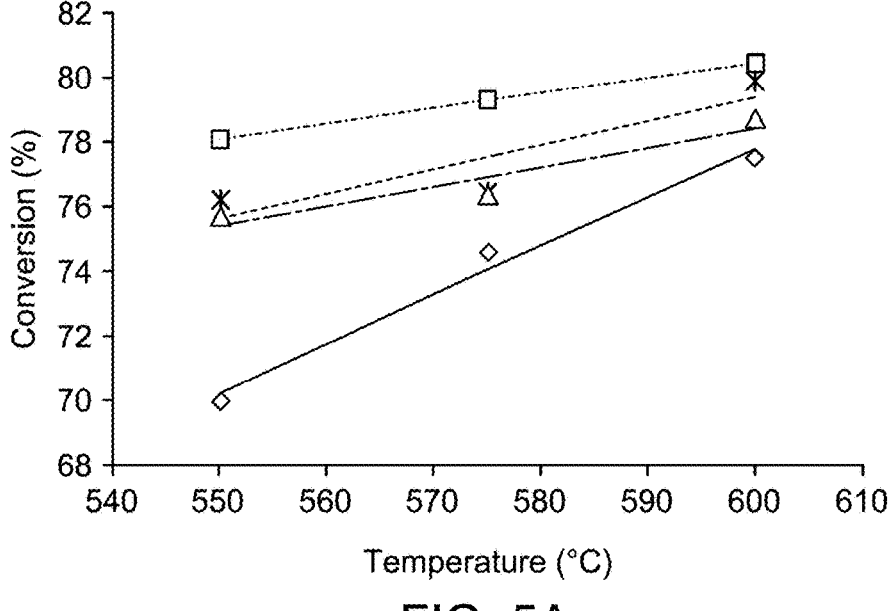
FIG. 5A shows the effect of temperature on conversion for different LDPE loadings in HVGO, according to certain embodiments.
Figure 5B:
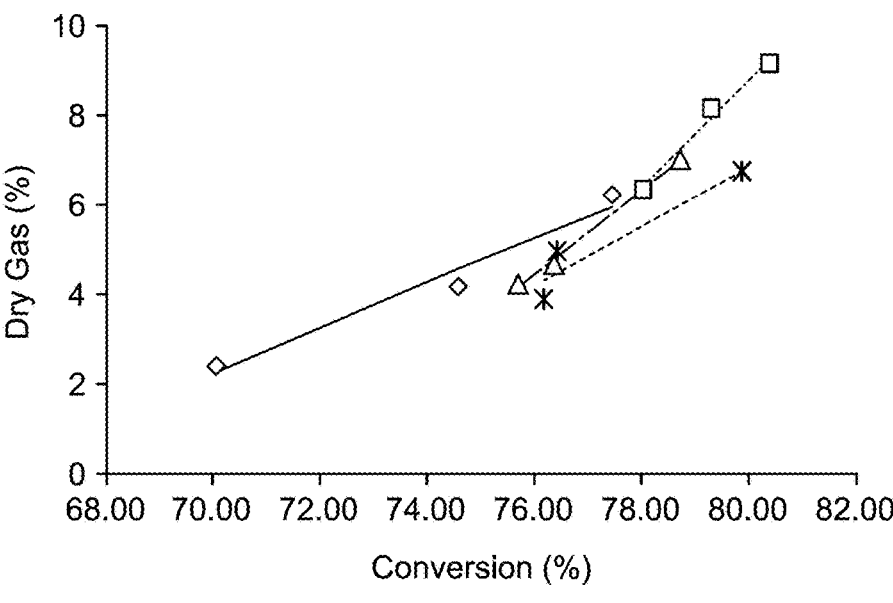
FIG. 5B shows the evolution of dry gas yields with conversion in the catalytic cracking of HVGO and LDPE/HVGO blends over E-Cat at a catalyst-to-oil ratio (C/O) of 5, according to certain embodiments.
Figure 5C:
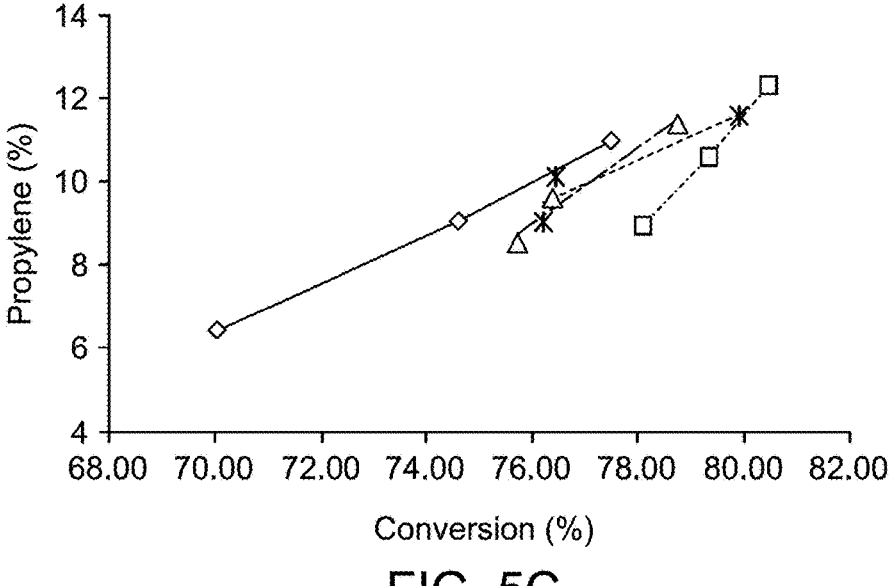
FIG. 5C shows the evolution of propylene yield with conversion in the catalytic cracking of HVGO and LDPE/HVGO blends over E-Cat at a catalyst-to-oil ratio (C/O) of 5, according to certain embodiments.
Figure 5D:
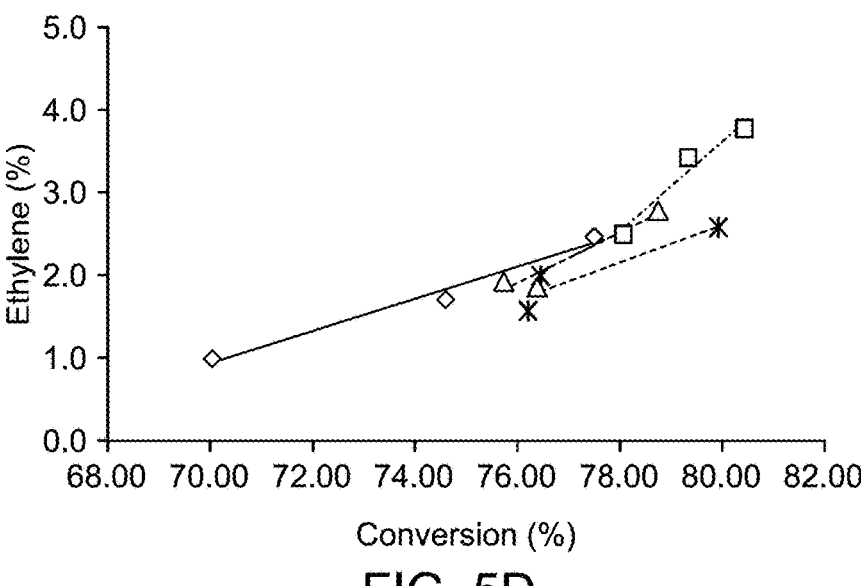
FIG. 5D shows the evolution of ethylene yield with conversion in the catalytic cracking of HVGO and LDPE/HVGO blends over E-Cat at a catalyst-to-oil ratio (C/O) of 5, according to certain embodiments.
Figure 5E:
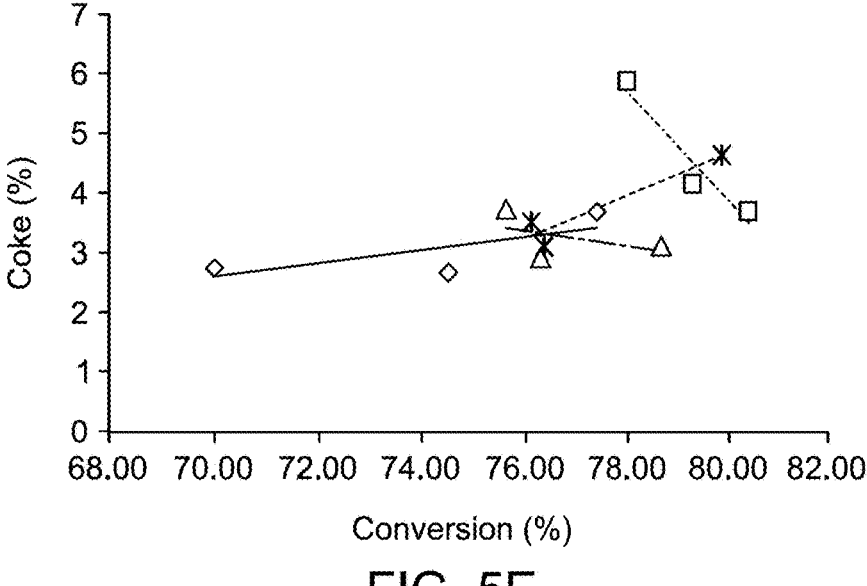
FIG. 5E shows the evolution of coke yield with conversion in the catalytic cracking of HVGO and LDPE/HVGO blends over E-Cat at a catalyst-to-oil ratio (C/O) of 5, according to certain embodiments.

The effect of temperature on the cracking of HVGO and LDPE blends over E-Cat was studied by varying the reactor temperature from 550° C. to 600° C. FIG. 5A depicts the conversion trend with temperature for the various feedstocks. At a temperature of 550° C., a significant increase in conversion was observed for the HVGO and LDPE/HVGO feeds. HVGO had a conversion of 70.0%, while 2.5 wt. % LDPE/HVGO and 10 wt. % LDPE/HVGO had 76.2% and 78.1% conversions, respectively. However, at 600° C., the HVGO conversion increased steeply while LDPE/HVGO conversion was only gradual, thus resulting in the convergence of conversion (%) within the range of 77.5% to 80.4% for all feedstocks. This may imply that at the higher temperature, some of the formed products underwent secondary reactions of oligomerization and aromatization to form heavy molecules that add to the heavy distillates of the respective LDPE dissolved feedstocks. These results explain why the HCO yields decreased slightly even though the LDPE/HVGO feedstocks have lower heavy distillates due to the 2.5-10 wt. % replacement of HVGO with LDPE.

The product yield evolution with conversion was studied by plotting the respective product yields over the conversions at various temperatures. The evolution of dry gas, propylene, and ethylene yields with respect to conversion plots are shown in FIG. 5B to FIG. 5F. It is observed that during catalytic cracking, dry gas, ethylene, and propylene yields showed a similar trend of increasing with an increase in feedstock conversion for all the LDPE/HVGO feedstocks. However, it is also clear, from the plots, that the level of increase in conversion is not the same for all the feedstocks. Notably, the HVGO feedstock showed the least amount of gas products (dry gas, ethylene, and propylene) at a minimum conversion of 70%, while the 10 wt. % LDPE/HVGO feedstock showed the largest amount of gas products at a minimum conversion of 76%. Similarly, it was observed that the gradients for the plot of 10 wt. % LDPE/HVGO in the gas products were higher than those of the HVGO feedstock, thus indicating that much higher gas product yield could be achieved at higher conversion conditions for the 10 wt. % LDPE/HVGO feedstocks than the HVGO feedstock.

Figure 5F:
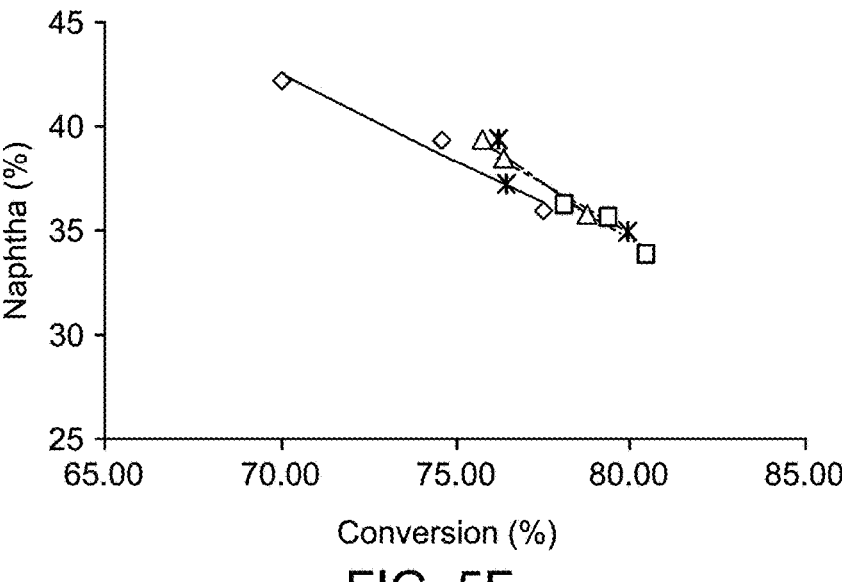
FIG. 5F shows the evolution of naphtha yield with conversion in the catalytic cracking of HVGO and LDPE/HVGO blends over E-Cat at a catalyst-to-oil ratio (C/O) of 5, according to certain embodiments.
Figure 6A:
FIG. 6A shows a performance comparison of E-Cat and E-Cat/ZSM-5(COM) catalysts, in terms of conversion trend, for the catalytic cracking of HVGO and LDPE/HVGO at 600° C. and a catalyst-to-oil ratio (C/O) of 5, according to certain embodiments.
Figure 6A:
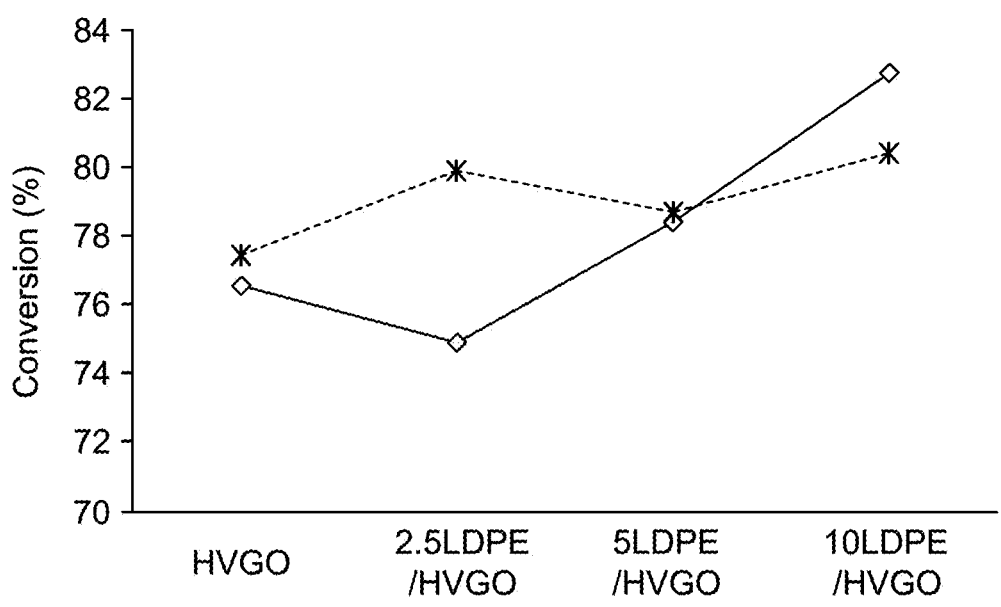
Figure 6B:
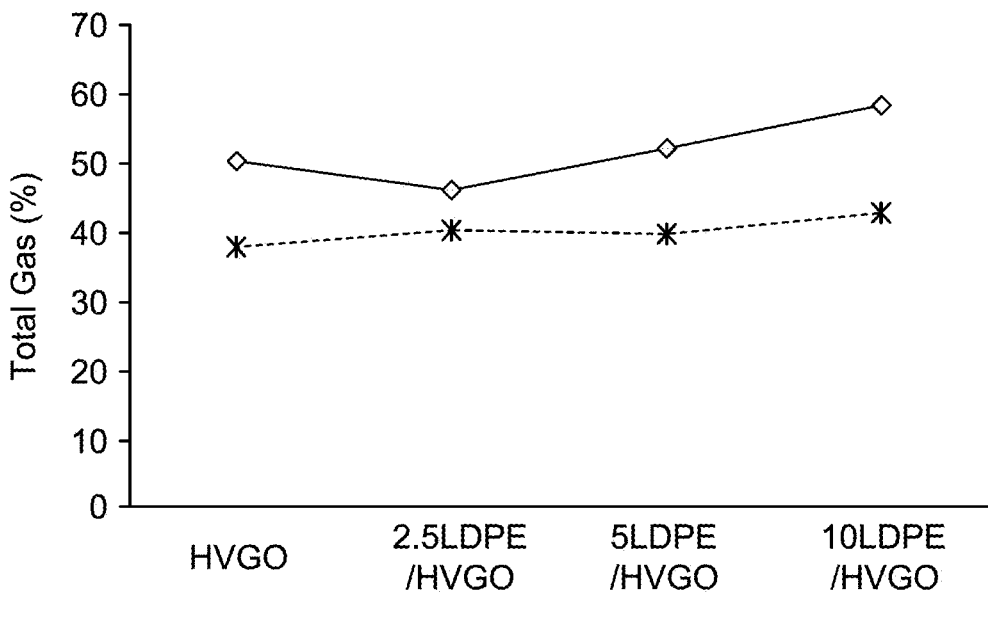
FIG. 6B shows a performance comparison of E-Cat and E-Cat/ZSM-5(COM) catalysts, in terms of total gas (%) yield, for the catalytic cracking of HVGO and LDPE/HVGO at 600° C. and a catalyst-to-oil ratio (C/O) of 5, according to certain embodiments.
Figure 6C:
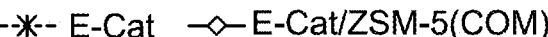
FIG. 6C shows a performance comparison of E-Cat and E-Cat/ZSM-5(COM) catalysts, in terms of dry gas (%) yield, for the catalytic cracking of HVGO and LDPE/HVGO at 600° C. and a catalyst-to-oil ratio (C/O) of 5, according to certain embodiments.
Figure 6C:
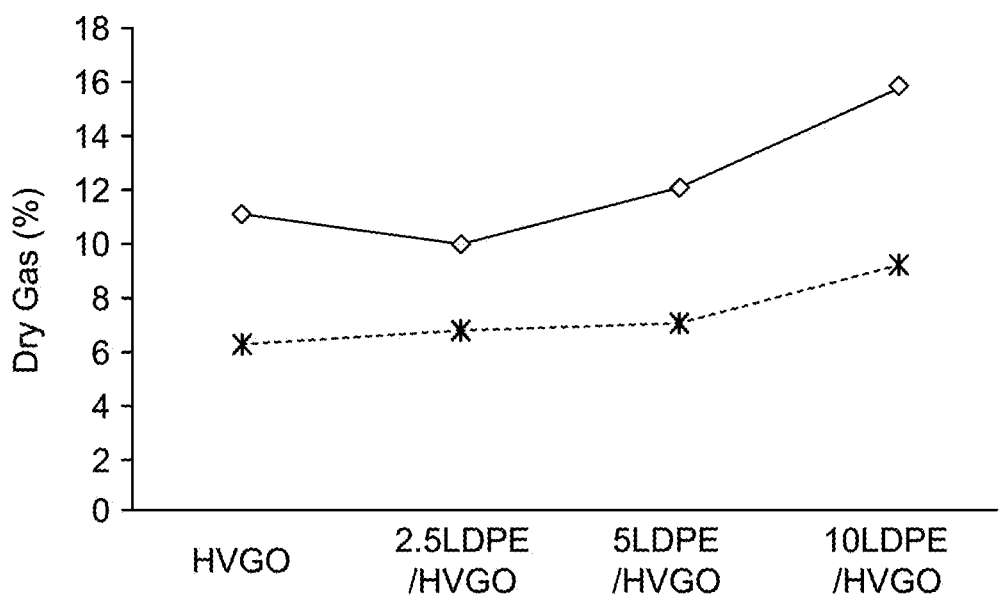
Figure 6D:
FIG. 6D shows a performance comparison of E-Cat and E-Cat/ZSM-5(COM) catalysts, in terms of $C_{2=}$-$C_{4=}$ (%) yield, for the catalytic cracking of HVGO and LDPE/HVGO at 600° C. and a catalyst-to-oil ratio (C/O) of 5, according to certain embodiments.
Figure 6D:
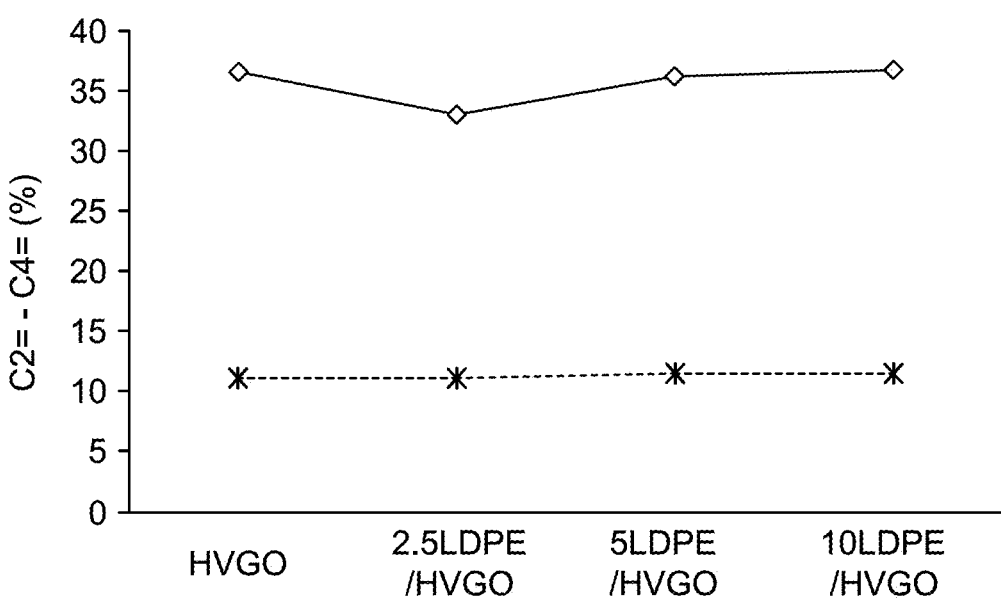
Figure 6E:
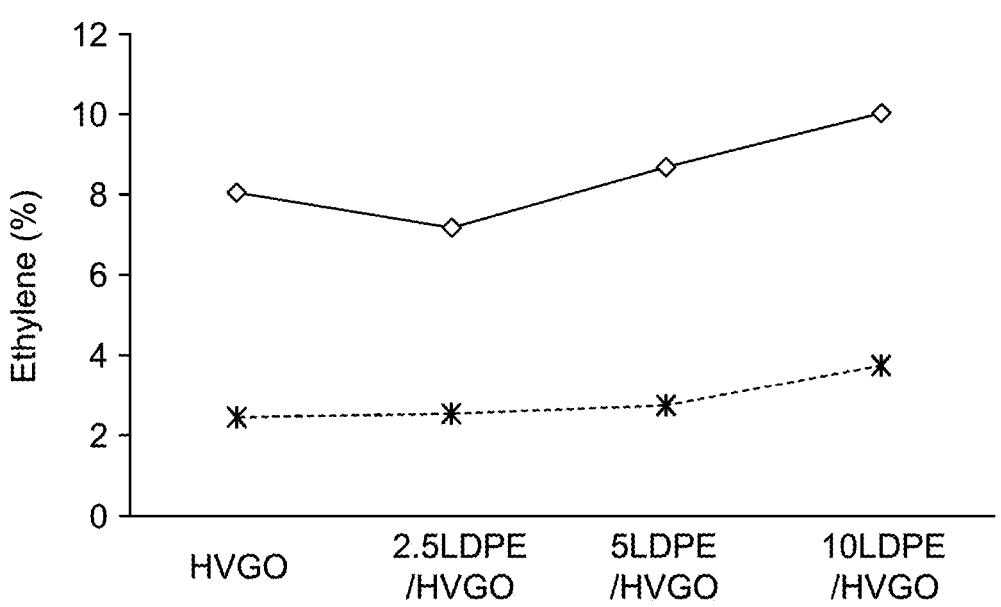
FIG. 6E shows a performance comparison of E-Cat and E-Cat/ZSM-5(COM) catalysts, in terms of ethylene (%) yield, for the catalytic cracking of HVGO and LDPE/HVGO at 600° C. and a catalyst-to-oil ratio (C/O) of 5, according to certain embodiments.
Figure 6F:
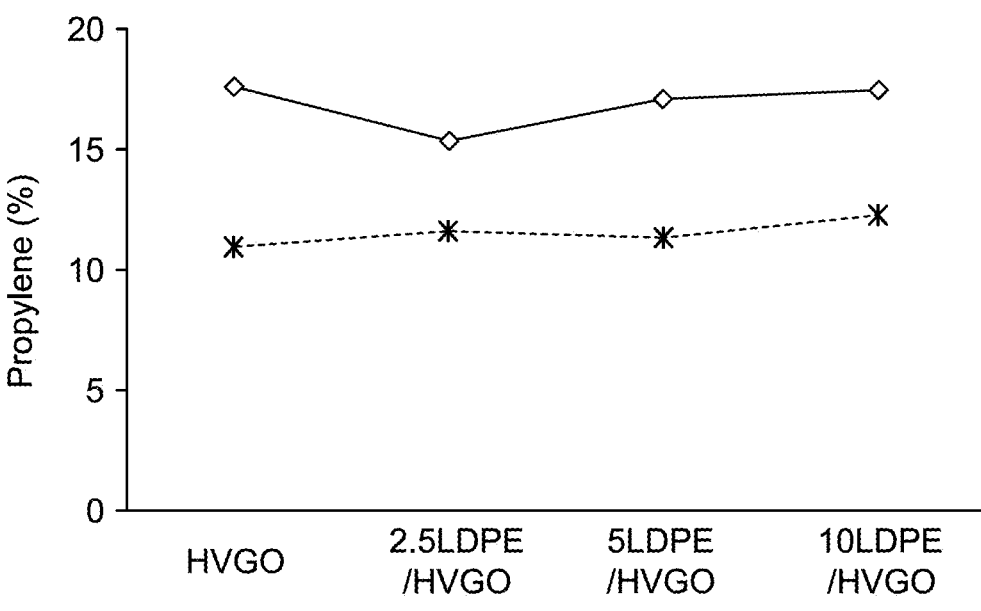
FIG. 6F shows a performance comparison of E-Cat and E-Cat/ZSM-5(COM) catalysts, in terms of propylene (%) yield, for the catalytic cracking of HVGO and LDPE/HVGO at 600° C. and a catalyst-to-oil ratio (C/O) of 5, according to certain embodiments.

The high yield of dry gas observed in the case of 10 wt. % LDPE/HVGO is partly due to the high yield of ethane and ethylene and not particularly due to methane and hydrogen. This shows that the depolymerization of LDPE in the HVGO feed yields more ethane and ethylene. Similarly, the propylene yield increases slightly from 11.0% in HVGO to 12.3% in 10 wt. % LDPE/HVGO. It is equally important to note that, although there was an increment in the yield of light olefins in the catalytic cracking of LDPE/HVGO feedstock, the molar ratio of C2=/C2 is almost the same in all the feedstocks, while the C3=/C3 molar ratio is slightly higher in the HVGO feedstock. This indicates that the cracking mechanism of LDPE/HVGO feedstock favors the formation of paraffins, which are not desirable in this study. Therefore, ZSM-5 zeolite as a light olefin selective catalyst, was added to the catalyst composition in the subsequent studies to increase the light olefin yield and decrease the formation of paraffins. The naphtha yield at various conversions is shown in FIG. 5F. It was observed that naphtha yield in all the feedstock decreased steadily with conversion, due to the increase in temperature. Usually, naphtha yield is expected to decrease with temperature, due to excessive cracking of the feedstock to form dry gas and LPG. As observed by Rodríguez et al. [See: Rodríguez, E., Gutiérrez, A., Palos, R., Vela, F. J., Azkoiti, M. J., Arandes, J. M., Bilbao, J., (2020a), "Co-cracking of high-density polyethylene (HDPE) and vacuum gas oil (VGO) under refinery conditions", Chemical Engineering Journal 382, 122602, the disclosure of which is incorporated herein by reference in its entirety], the yield of heavy n-paraffins (naphtha) decreases with increasing temperature, since the cracking of the heaviest molecules is favored, leading to the formation of lighter n-paraffins and olefins in the range of dry gas and LPG fractions. In addition, the hydrogen-transfer reactions, responsible for converting olefins into n-paraffins, are disfavored at high temperatures. This implies that the co-feeding of LDPE did not facilitate the cracking of heavy oil components of the HVGO to form more paraffins, especially at higher conversion (higher temperature).

Cracking over E-Cat/ZSM-5(COM): The effect of commercial ZSM-5 additive, ZSM-5(COM), on the conversion and product distribution in the co-cracking of LPDE with HVGO was further studied by cracking 1 gram of the respective feeds over 5 grams of E-Cat/ZSM-5(COM) catalyst formulation at reactor temperature of 600° C. and a 30 second feed injection time. The E-Cat/ZSM-5(COM) catalyst consists of 85% E-Cat and 15% commercial ZSM-5 additive.

FIG. 6A to FIG. 6F shows the performance comparison plot for all the studied feedstocks under the selected reaction conditions. Compared to the cracking reaction over E-Cat, the HVGO cracking over E-Cat/ZSM-5(COM) shows a slight decrease in conversion—from 77.5% to 76.6%—as presented in FIG. 6A. The E-Cat, herein a USY zeolite, has a large pore size that enhances the accessibility of its active sites by the large molecules of HVGO. However, after substituting 15% of the E-Cat with ZSM-5(COM), the relatively small pore size of ZSM-5(COM) creates a diffusion limitation for the HVGO, and this slightly decreases its conversion; on the other hand, the ZSM-5(COM) shape selectivity to light olefins increases the total gas yield, and the light olefins yield as shown in FIG. 6B to FIG. 6F.

The blending of HVGO with LDPE shows a general trend of increasing conversion and gas product yield. The LDPE is a linear structure that consists of repeated monomers made from carbon and hydrogen atoms. Typically, the substitution of various weight percent of HVGO with LDPE to form LDPE/HVGO blends resulted in a dilution of heavy molecules that are present in the HVGO feed, which addresses the challenge of diffusion limitation observed in the E-Cat/ZSM-5(COM) catalyst. This effect is more pronounced in the higher loading of LDPE, particularly the 10 wt. %

LDPE/HVGO feedstock, where a substantial increase in both conversion and total gas product yield is observed.

Figure 7A:
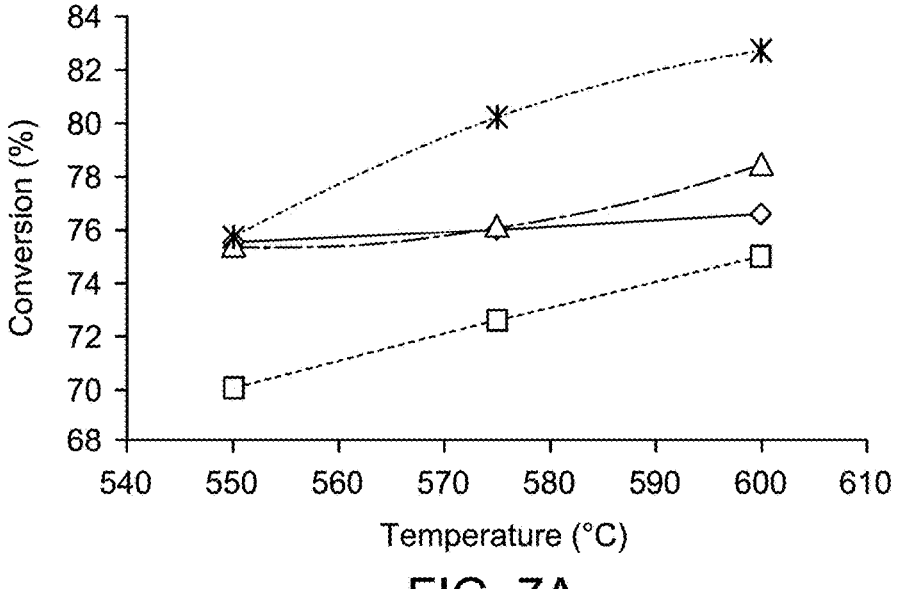
FIG. 7A shows the effect of temperature on conversion in the catalytic cracking of HVGO and HVGO/LDPE blends over E-Cat/ZSM-5(COM) catalyst at a catalyst-to-oil ratio (C/O) of 5, according to certain embodiments.
Figure 7B:
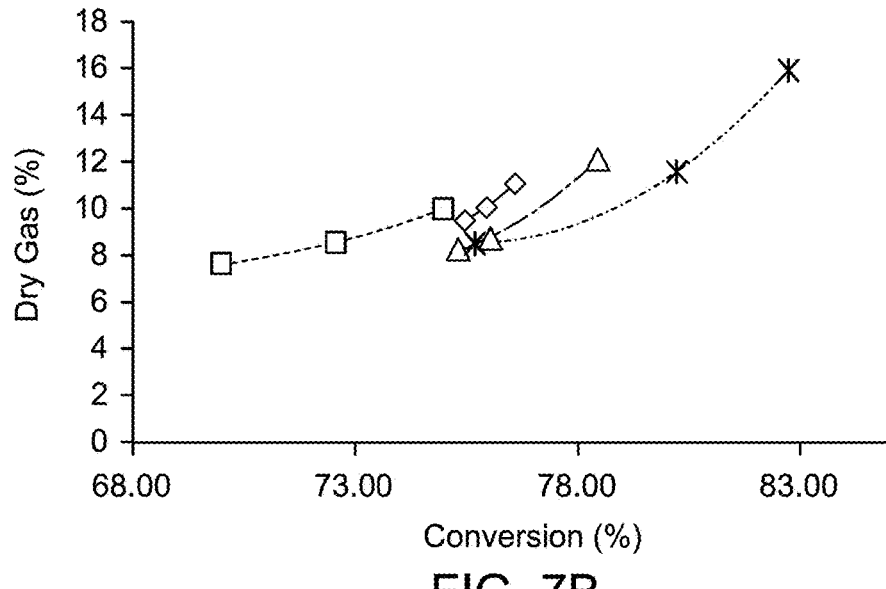
FIG. 7B shows the yields of dry gas (%) with conversion in the catalytic cracking of HVGO and HVGO/LDPE blends over E-Cat/ZSM-5(COM) catalyst at a catalyst-to-oil ratio (C/O) of 5, according to certain embodiments.
Figure 7C:
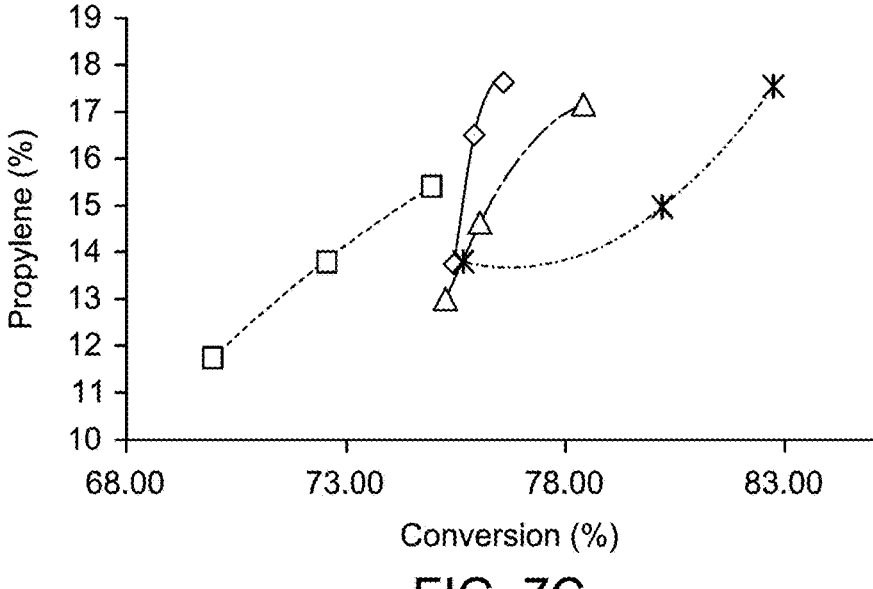
FIG. 7C shows the yields of propylene (%) with conversion in the catalytic cracking of HVGO and HVGO/LDPE blends over E-Cat/ZSM-5(COM) catalyst at a catalyst-to-oil ratio (C/O) of 5, according to certain embodiments.
Figure 7D:
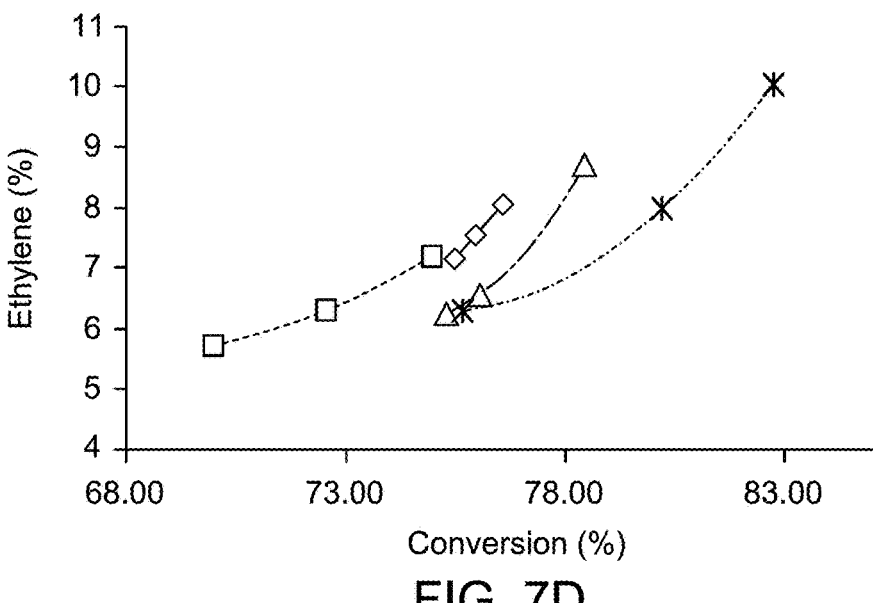
FIG. 7D shows the yields of ethylene (%) with conversion in the catalytic cracking of HVGO and HVGO/LDPE blends over E-Cat/ZSM-5(COM) catalyst at a catalyst-to-oil ratio (C/O) of 5, according to certain embodiments.
Figure 7E:
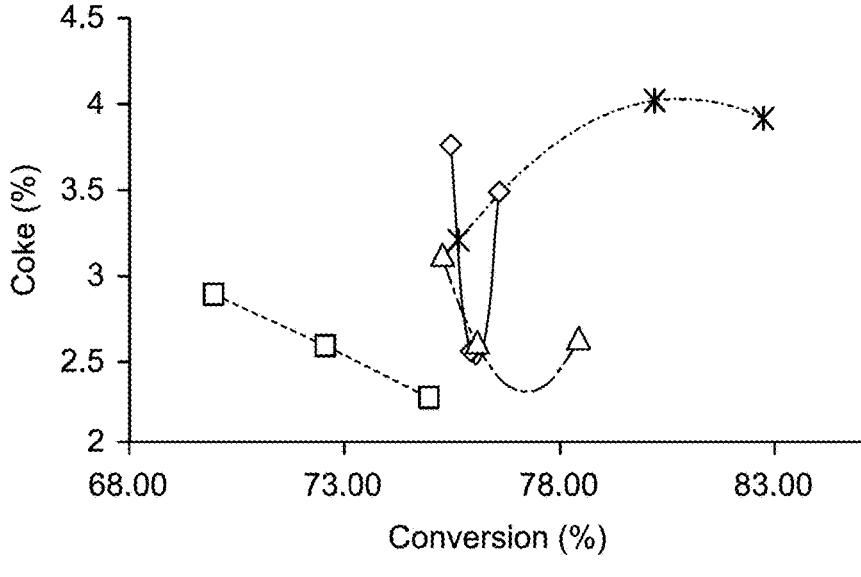
FIG. 7E shows the yields of coke (%) with conversion in the catalytic cracking of HVGO and HVGO/LDPE blends over E-Cat/ZSM-5(COM) catalyst at a catalyst-to-oil ratio (C/O) of 5, according to certain embodiments.
Figure 7F:
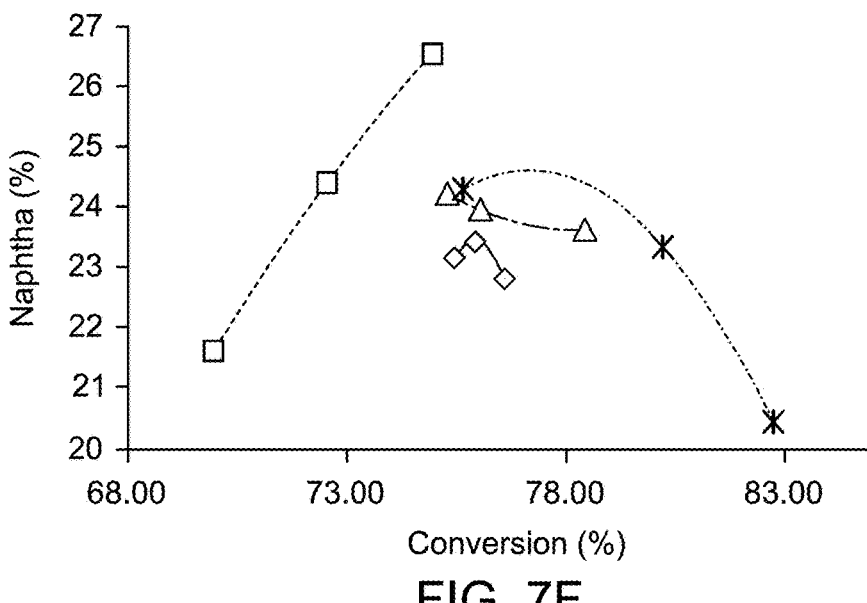
FIG. 7F shows the yields of naphtha (%) with conversion in the catalytic cracking of HVGO and HVGO/LDPE blends over E-Cat/ZSM-5(COM) catalyst at a catalyst-to-oil ratio (C/O) of 5, according to certain embodiments.

The effect of temperature on the catalytic cracking of HVGO and blends over E-Cat/ZSM-5(COM) catalyst was studied by varying the reactor temperature from 550° C. to 600° C. FIG. 7A depicts the conversion trend with temperature for the various feedstocks. Typically, the conversion is expected to increase with temperature for an endothermic reaction, such as the cracking of HVGO. However, the presence of a catalyst affects the cracking route, and competition between the radical reaction pathway and the bimolecular cracking route occurs depending on the nature of the catalyst. In the case of E-Cat, the conversion increases proportionately with temperature; however, in the case of E-Cat/ZSM-5(COM), only a slight increase in conversion was noted with an increase in temperature, which indicates that even at higher temperatures, the middle and heavy distillates do not decrease significantly during the cracking of HVGO. This is ascribed to the low external surface area of the ZSM-5(COM) that inhibits the interaction of the heavy distillates in HVGO with the active sites of the zeolites, even at higher temperatures. Consequently, the coke yield showed a curvature trend, with about 3.76% at 550° C. decreasing to 2.53% at 575° C. and increasing to 3.49% at 600° C. (FIG. 7E). At a reactor temperature of 550° C., the cracking was not complete, which resulted in deposition of feed components on the catalyst which were later converted to coke; as the reactor temperature increased to 575° C., more cracking occurred which reduces the feed component deposition on the catalyst channels, and at higher reactor temperature of 600° C., the oligomerization and aromatization further led to increased coke formation. Although the addition of LDPE to HVGO showed an overall increase in both conversion and selectivity to light olefins (FIG. 7C and FIG. 7D), naphtha (FIG. 7F), and dry gas (FIG. 7B), the trend in the cracking of 2.5 wt. % LDPE/HVGO over E-Cat/ZSM-5(COM) showed that addition of 2.5 wt. % LDPE slightly decreased both conversion and light olefins yield at all the cracking temperatures.

Cracking over E-Cat/mesoporous ZSM-5: Three ZSM-5 catalysts, ZSM-5(25), ZSM-5(50), and ZSM-5(75) were employed with E-Cat for the cracking of 2.5 wt. % LDPE/HVGO feed, and the results were compared with that of E-Cat/ZSM-5(COM). FIG. 8 shows the comparison plots for E-Cat, E-Cat/ZSM-5(COM), and E-Cat/ZSM-5(50). The 2.5 wt. % LDPE/HVGO cracking over E-Cat/ZSM-5(COM) shows lower conversion (75.0%) than the E-Cat (80.0%), and this was ascribed to the diffusion limitation that resulted due to the pore size of ZSM-5(COM) additive. In the case of mesoporous ZSM-5(50) zeolite, the conversion increases to 83.7%. The total gas yield increased with the addition of ZSM-5, and it was observed that ZSM-5(50) produced a slightly higher total gas yield (of 47.4%) compared to ZSM-5(COM), which had a total gas yield of 46.1%. This was accompanied by a total liquid product yield of 55.0%, 51.7%, and 47.9% in E-Cat, E-Cat/ZSM-5(COM), and E-Cat/ZSM-5(50), respectively. Typically, a low yield of liquid product and coke indicates an effective cracking reaction. However, the composition of liquid products also indicates the catalyst's performance. Thus, the comparison of the yields of naphtha, LCO, and HCO in the catalytic cracking of 2.5 wt. % LDPE/HVGO over the three different catalysts is also presented in FIG. 8A.

The yield of naphtha, LCO, and HCO during the cracking of 2.5 wt. % LDPE/HVGO over E-Cat is 35%, 12.9%, and 7.2%, while for the cracking reaction over E-Cat/ZSM-5 (COM), the yields are 26.6%, 10.9%, and 14.1% respectively. As expected, the ZSM-5(COM) has a pore structure that has shape selectivity for paraffins, which results in further cracking of the formed naphtha to gas products; however, the small external surface area of the zeolite limits the cracking of the heavy distillates of the HVGO which result in the observed high yield of HCO in the E-Cat/ZSM-5(COM) catalyst. Interestingly, the cracking reaction over E-Cat/ZSM-5(50) gives a high yield of naphtha (31.5%) and a low yield of LCO (10.5%) and HCO (5.9%). This is ascribed to: the mesoporous surface area and pore structure of the ZSM-5(50) additive that enhance the diffusion of the heavy distillates in HVGO to the zeolite active sites for cracking; and, to the small amount of strong acid sites, which prevent secondary cracking reactions that consume the light olefins via excess cracking, hydrogen transfer or aromatization to form more dry gas and polycyclic aromatics that increase the yield of HCO and coke formation.

Figure 8A:
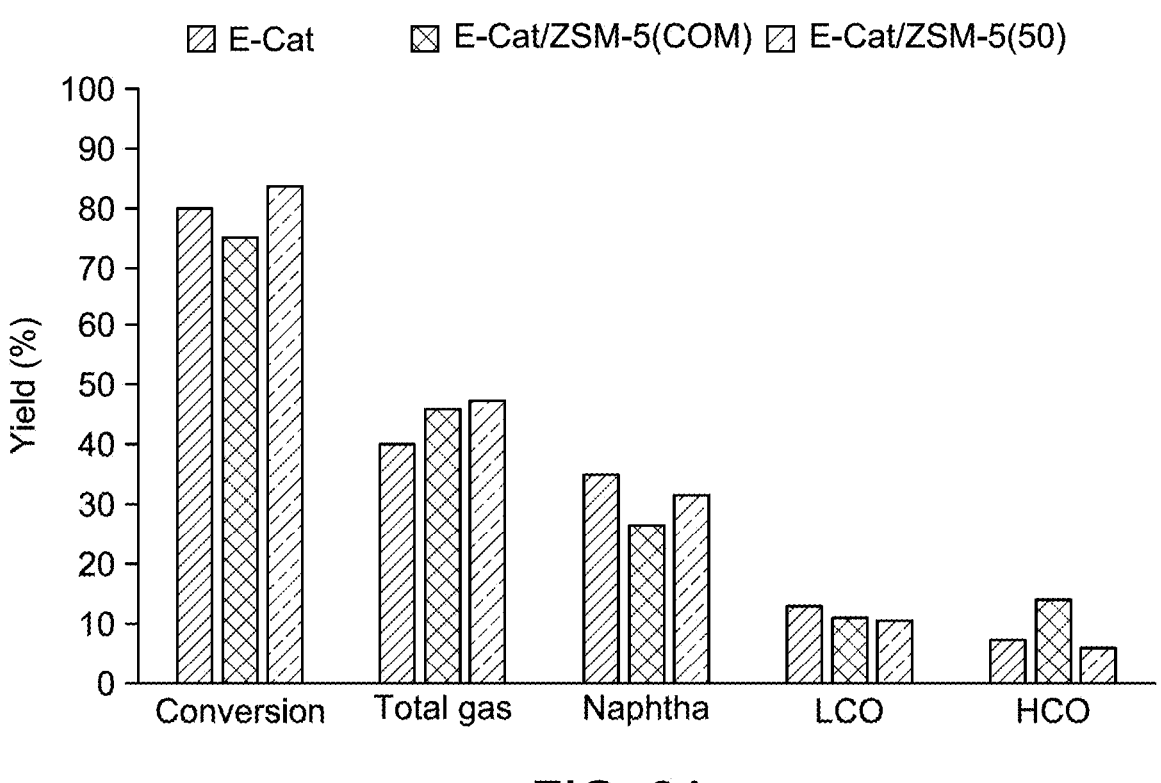
FIG. 8A shows the effect of catalytic cracking of 2.5LDPE/HVGO feed on conversion and product distribution at a temperature of 600° C. over different catalyst compositions, according to certain embodiments.
Figure 8B:
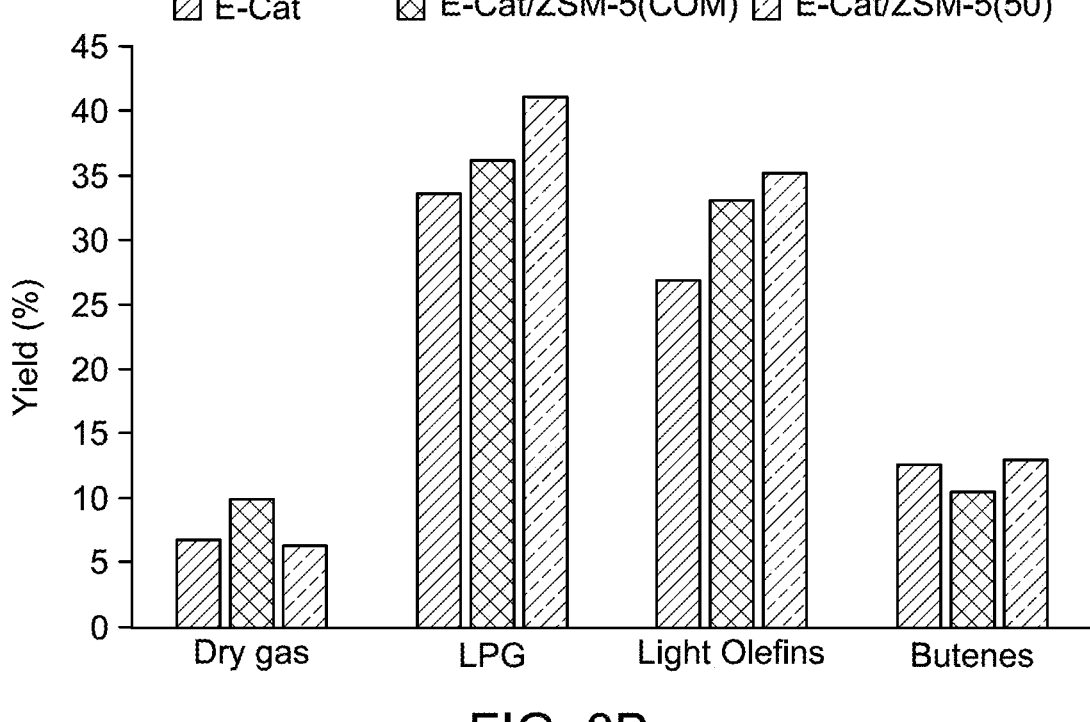
FIG. 8B shows the effect of catalytic cracking of 2.5LDPE/HVGO feed on total gas product distribution at a temperature of 600° C. over different catalyst compositions, according to certain embodiments.
Figure 8C:
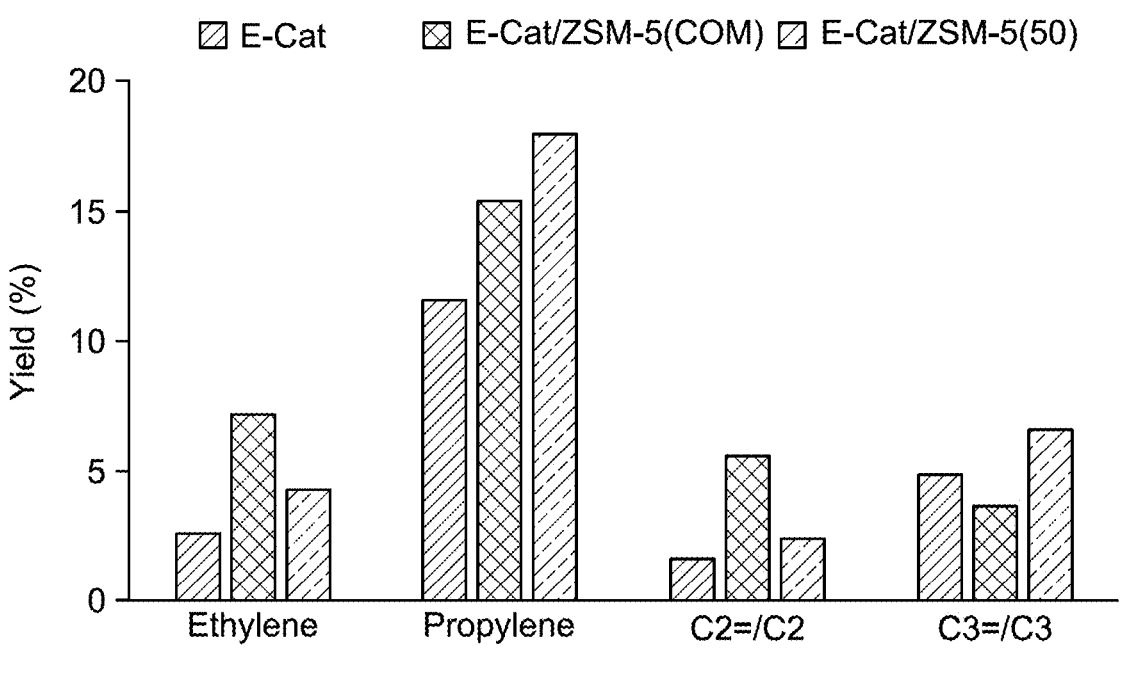
FIG. 8C shows the effect of catalytic cracking of 2.5LDPE/HVGO feed on light olefins distribution at a temperature of 600° C. over different catalyst compositions, according to certain embodiments.

FIG. 8B shows the trend in gas product yield, which increases for cracking over E-Cat/ZSM-5(COM) due to the over-cracking of methane and ethane. However, the cracking reaction over E-Cat and E-Cat/ZSM-5(50) yields almost the same amount of dry gas. This confirms the textural property and moderate acidity advantages of the mesoporous ZSM-5(50) over the ZSM-5(COM). Similarly, the LPG and total light olefins yield show a clear improvement trend in the catalyst performance, with the E-Cat/ZSM-5(50) giving the highest yield and E-Cat giving the lowest yield. The light olefins trend is further presented in FIG. 8C, and it is observed that E-Cat/ZSM-5(COM) forms a high yield of ethylene whereas the E-Cat/ZSM-5(50) forms higher yield of propylene. Thus, as presented in Table 3, the $C_{3=}/C_3$ ratio is higher for the E-Cat/ZSM-5(50), while the $C_{2=}/C_2$ is higher for the E-Cat/ZSM-5(COM). This implies that the catalyst composition plays a role in modulating the reaction pathway for forming light olefins. The small pore size of the ZSM-5(COM) additive in the E-Cat/ZSM-5(COM) may cause steric hindrance to the classical catalytic cracking route, thereby forcing the reaction to proceed via the protolytic (monomolecular) pathways with the formation of more dry gas as shown in Table 3 herein below.

TABLE 3

Effect of mesoporous ZSM-5 addition on the conversion and product distribution for the catalytic cracking of 2.5 wt. % LDPE/HVGO at 600° C. and Catalyst: Oil Ratio of 5

| Catalyst | E-Cat/ ZSM- 5(COM) | E-Cat/ ZSM- 5(25) | E-Cat/ ZSM- 5(50) | E-Cat/ ZSM- 5(75) |
|---|---|---|---|---|
| Mass balance | 101 | 96.6 | 98.2 | 97.6 |
| Conversion (%) | 75.0 | 75.5 | 83.7 | 81.1 |
| Product yields (wt. %) | | | | |
| H₂ | 0.12 | 0.02 | 0.03 | 0.03 |
| C1 | 1.29 | 0.27 | 0.07 | 0.02 |
| C2 | 1.39 | 1.19 | 1.93 | 1.49 |
| C2= | 7.18 | 3.55 | 4.27 | 4.79 |
| C3 | 4.41 | 2.20 | 2.84 | 3.13 |
| C3= | 15.4 | 14.7 | 17.9 | 19.9 |
| iC4 | 4.23 | 4.68 | 5.99 | 6.54 |
| nC4 | 1.64 | 1.06 | 1.38 | 1.49 |
| t2C4= | 2.27 | 2.63 | 3.20 | 3.30 |
| 1C4= | 1.88 | 2.14 | 2.67 | 2.74 |
| iC4= | 3.78 | 3.84 | 4.26 | 4.84 |
| c2C4= | 1.86 | 2.16 | 2.64 | 2.75 |
| 1,3-BD | 0.06 | 0.41 | 0.07 | 0.08 |
| C4 in Liquid | 0.65 | 0.44 | 0.11 | 0.04 |
| Total Gas | 46.1 | 39.2 | 47.4 | 51.1 |
| Naphtha | 26.6 | 32.3 | 31.5 | 25.9 |
| LCO | 10.9 | 14.9 | 10.5 | 12.1 |

TABLE 3-continued

Effect of mesoporous ZSM-5 addition on the conversion and product distribution for the catalytic cracking of 2.5 wt. % LDPE/HVGO at 600° C. and Catalyst: Oil Ratio of 5

| Catalyst | E-Cat/ ZSM- 5(COM) | E-Cat/ ZSM- 5(25) | E-Cat/ ZSM- 5(50) | E-Cat/ ZSM- 5(75) |
|---|---|---|---|---|
| HCO | 14.1 | 9.58 | 5.87 | 6.80 |
| Coke | 2.27 | 3.96 | 4.74 | 4.02 |
| Groups (wt. %) | | | | |
| H2-C2 (dry gas) | 9.98 | 5.02 | 6.30 | 6.33 |
| C3-C4 (LPG) | 36.2 | 34.2 | 41.1 | 44.8 |
| C2-C4 (Light olefins) | 33.1 | 29.8 | 35.2 | 38.4 |
| C3= + C4= | 25.9 | 26.3 | 30.9 | 33.7 |
| C4 butenes | 10.5 | 11.6 | 12.9 | 13.7 |
| Molar ratio (mol/mol) | | | | |
| C2=/C2 | 5.53 | 3.20 | 2.37 | 3.45 |
| C3=/C3 | 3.65 | 6.97 | 6.62 | 6.66 |
| C4=/C4 | 1.85 | 2.10 | 1.82 | 1.77 |
| iC4=/C4= | 0.36 | 0.33 | 0.33 | 0.35 |
| iC4=/iC4 | 0.93 | 0.85 | 0.74 | 0.77 |

On the other hand, the relatively large pore size of ZSM-5(50) zeolite in the E-Cat/ZSM-5(50) favors the classical catalytic cracking pathway, consuming the available alkenes—mostly ethylene—that were formed via thermal cracking at the high reactor temperature.

Figure 8D:
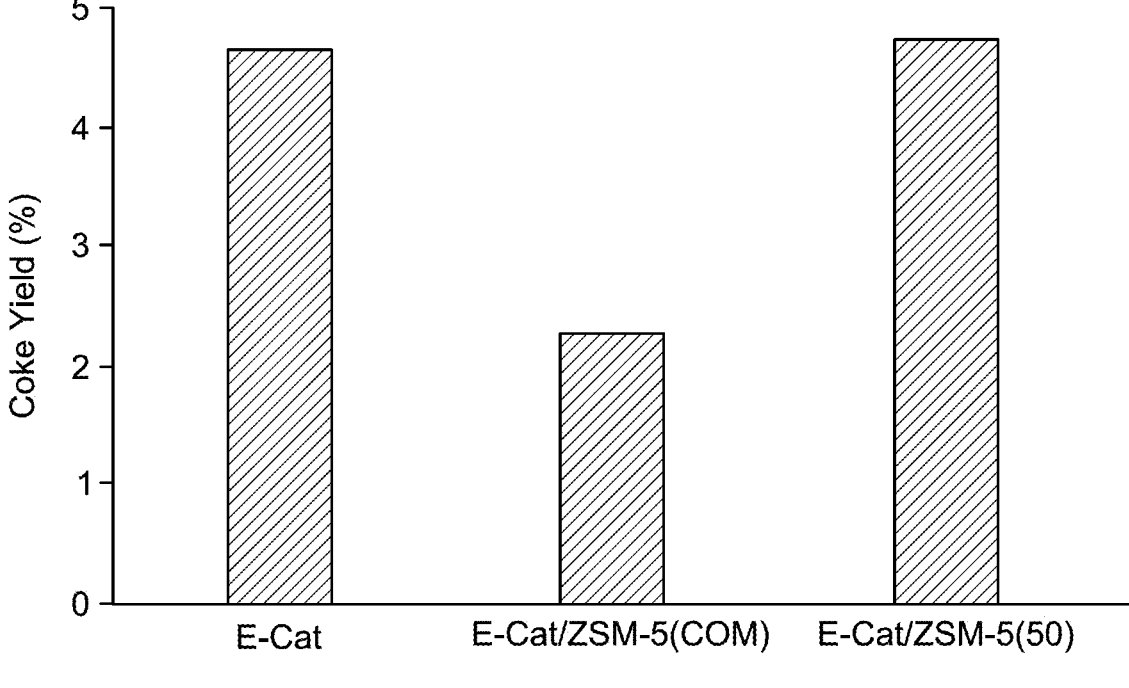
FIG. 8D shows the effect of catalytic cracking of 2.5LDPE/HVGO feed on coke yield at a temperature of 600° C. over different catalyst compositions, according to certain embodiments.

FIG. 8D shows approximately similar coke yield for the E-Cat and E-Cat/ZSM-5(50), while the E-Cat/ZSM-5 (COM) shows lower coke yield. Since coke is also required for maintaining the heat balance of the regenerator in the FCC unit [See: Amblard, B., Singh, R., Gbordzoe, E., Raynal, L., (2017), *CFD modeling of the coke combustion in an industrial FCC regenerator. Chem. Eng. Sci.* 170, 731-742, the disclosure of which is incorporated herein by reference in its entirety]. A coke yield of up to 5% may be considered within the acceptable range. Thus, the synthesized mesoporous ZSM-5(50) is considered to be a better catalyst additive than the ZSM-5(COM), and further studies were carried out into the role of the Si/Al ratio of the synthesized ZSM-5.

Figure 9A:
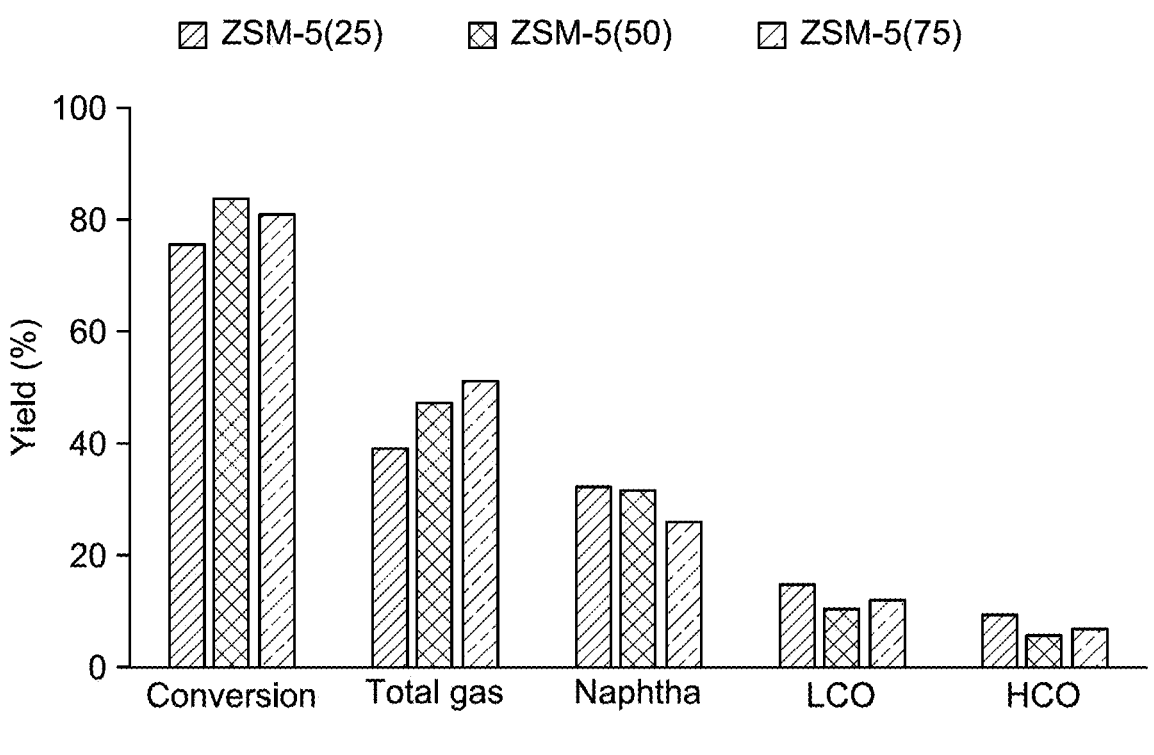
FIG. 9A shows the effect of catalytic cracking of 2.5LDPE/HVGO feed at a temperature of 600° C. over E-Cat/ZSM-5(x), wherein x=25, 50, and 75, on conversion and product distribution, according to certain embodiments.
Figure 9B:
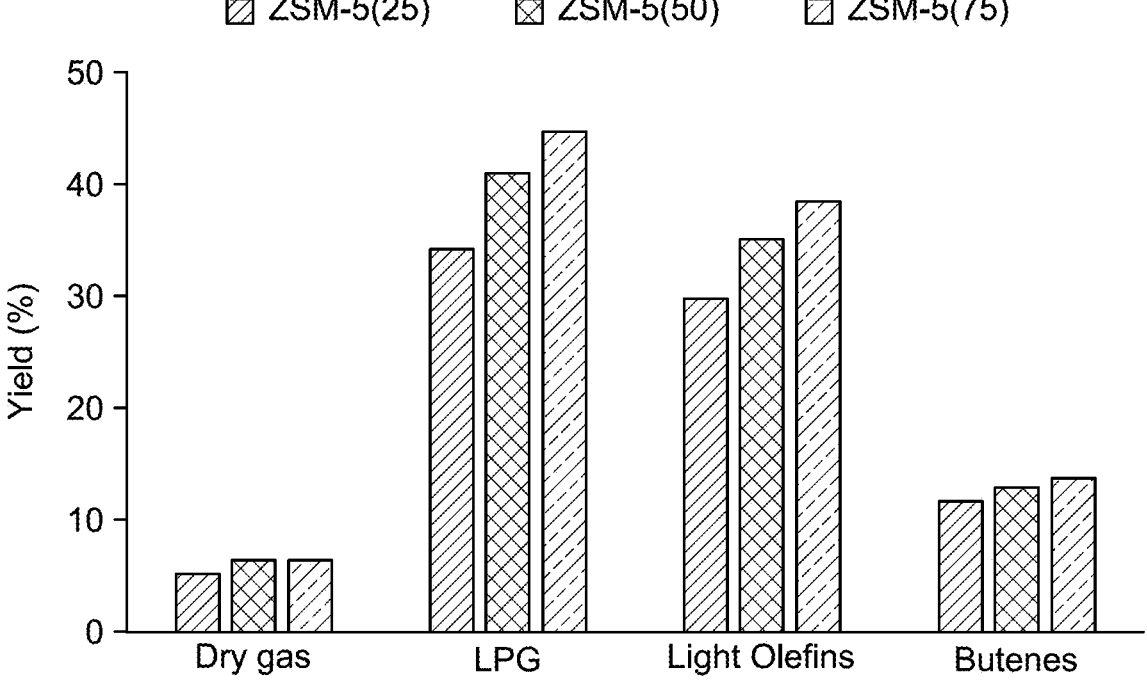
FIG. 9B shows the effect of catalytic cracking of 2.5LDPE/HVGO feed at a temperature of 600° C. over E-Cat/ZSM-5(x), wherein x=25, 50, and 75, on total gas product distribution, according to certain embodiments.

As shown in FIG. 9A, the catalytic cracking of 2.5 wt. % LDPE/HVGO over E-Cat/ZSM-5(25) gives 75.5% conversion, similar to the conversion obtained using E-Cat/ZSM-5(COM). However, the cracking over E-Cat/ZSM-5(50) and E-Cat/ZSM-5(75) showed increased conversion of up to 83.7% and 81.1%, respectively. Although ZSM-5(25) has the largest surface area of 349 m²/g compared to ZSM-5(50) (316 m²/g), the ZSM-5(25) has small mesopore volume (0.079 cm³/g) with $V_{Meso}/V_{Micro}$ of 1.03, while the ZSM-5 (50) has relatively large mesopore volume of 0.18 cm³/g and $V_{Meso}/V_{Micro}$ of 2.53. Additionally, the pore size of ZSM-5 (25) is 2.22 nm, while the pore size of ZSM-5(50) is 5.59 nm. This could be responsible for the increased conversion during the catalytic cracking of 2.5 wt. % LDPE/HVGO over the E-Cat/ZSM-5(50). However, the E-Cat/ZSM-5(75) has a slightly lower conversion than E-Cat/ZSM-5(50), although it has a large BET surface area and mesopore surface area. This is related to the lower $V_{Meso}/V_{Micro}$ and pore size of the ZSM-5(75) additive compared to the ZSM-5(50). The product distribution shows that the E-Cat/ZSM-5(75) gives the highest amount of total gas (51.1%), while the E-Cat/ZSM-5(25) gives the lowest total gas yield (39.2%). The total gas yield indicates a catalyst's cracking performance, and this is often correlated with the catalyst's textural properties and accessible acid sites.

The ZSM-5(25) is expected to have more acid sites than its higher Si/Al ratio counterparts. However, the $NH_3$-TPD result shows that the ZSM-5(25) has a total acidity of 0.294 mmol/g that comprises weak acid sites (0.154 mmol/g) and strong acid sites (0.140 mmol/g). This probably happens as a result of extra-framework aluminum that accumulates inside the zeolite cavity and blocks the pore's entrance, as observed in the small mesopore volume and pore size, thus reducing the accessible acid sites of the zeolites [See: Sandoval-Díaz, L. E., González-Amaya, J. A., Trujillo, C. A., (2015). *"General aspects of zeolite acidity characterization. Microporous and Mesoporous Materials"*, 215, 229-243, the disclosure of which is incorporated herein by reference in its entirety]. Thus, the fast-aging approach for synthesizing ZSM-5(25) affects the complete coordination of aluminum into the zeolite framework. Moreover, medium-strength acid sites have been linked with high activity and selectivity for polyolefin degradation [See: Serrano, D. P., Aguado, J., Escola, J. M., (2000), *"Catalytic cracking of a polyolefin mixture over different acid solid catalysts"*, Ind. Eng. Chem. Res. 39, 1177-1184, the disclosure of which is incorporated herein by reference in its entirety]. Therefore, the absence of medium-strength acid sites may hinder the cracking of the LDPE, which is manifested in the relatively low conversion and total gas yield.

Figure 9C:
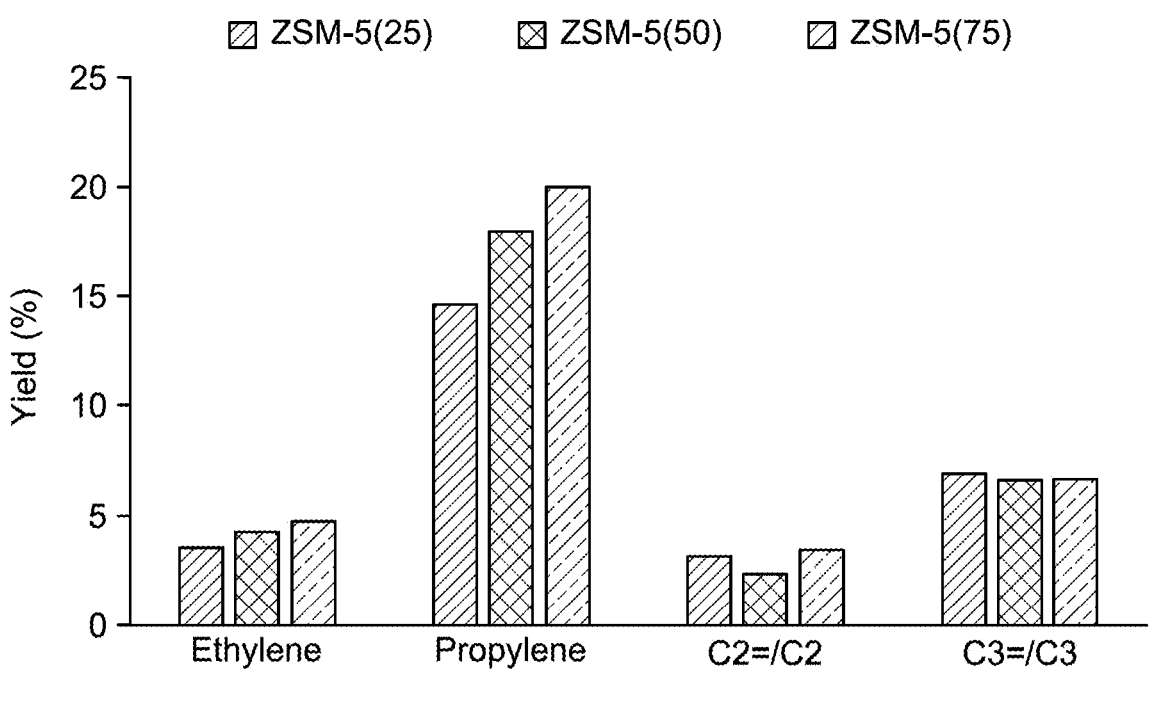
FIG. 9C shows the effect of catalytic cracking of 2.5LDPE/HVGO feed at a temperature of 600° C. over E-Cat/ZSM-5(x), wherein x=25, 50, and 75, on light olefins distribution, according to certain embodiments.

The E-Cat/ZSM-5(25) gave a higher yield of naphtha, LCO, and HCO, while the E-Cat/ZSM-5(75) gave a lower yield of naphtha and slightly higher yield of LCO and HCO in comparison with E-Cat/ZSM-5(50). The relatively low yield of LCO and HCO of E-Cat/ZSM-5(50) in comparison to E-Cat/ZSM-5(75) can be attributed to the larger pore size and accessible acid sites of the E-Cat/ZSM-5(50) and its relatively small crystal size [See: Mohamed, H. O., Parsapur, R. K., Hita, I., Cerrillo, J. L., Ramírez, A., Huang, K. W., Gascon, J., Castaño, P., (2022), *"Stable and reusable hierarchical ZSM-5 zeolite with superior performance for olefin oligomerization when partially coked"*, Appl. Catal. B, 316, 121582, the disclosure of which is incorporated herein by reference in its entirety]. FIG. 9 B presents an analysis of the total gas yield. Although the dry gas yield is almost the same (6.3%) for E-Cat/ZSM-5(50) and E-Cat/ZSM-5(75), the LPG and light olefins yield were higher in the E-Cat/ZSM-5(75) system. The E-Cat/ZSM-5(25) gave a slightly lower dry gas yield (5.0%), which can be correlated to its low total gas yield. Similarly, as shown in FIG. 9C, the E-Cat/ZSM-5(75) yielded 4.8% ethylene and 19.9% propylene, which is higher than the yields for the other catalyst formulations. The E-Cat/ZSM-5(50) formulation gave 4.3% and 17.9%, while E-Cat/ZSM-5(25) gives 3.6% and 14.6% respectively.

The ZSM-5(50) has higher acidity (0.686 mmol/g). However, the acid sites are largely weak acid sites that promote the formation of naphtha range products, and this is responsible for the high yield of naphtha for cracking of 2.5 wt. % LDPE/HVGO over E-Cat/ZSM-5(50). On the other hand, the ZSM-5(75) has strong acid sites (0.107 mmol/g) that further crack the naphtha range to light olefins, and this is supported by the optimum pore dimension of ZSM-5(75) that hinders diffusion of the naphtha range product out of the zeolite internal cavity, thus exposing them to the strong acid sites for selective cracking to light olefins.

Figure 9D:
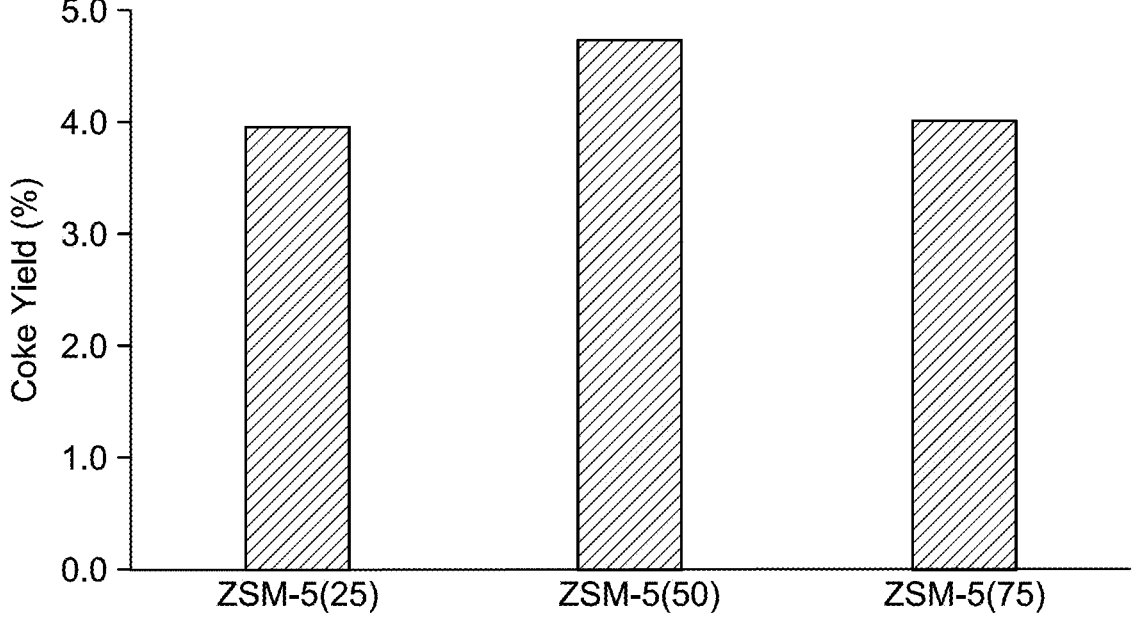
FIG. 9D shows the effect of catalytic cracking of 2.5LDPE/HVGO feed at a temperature of 600° C. over E-Cat/ZSM-5(x), wherein x=25, 50, and 75 on coke yield, according to certain embodiments.

The result of the coke yield is presented in FIG. 9D, and it was noted that E-Cat/ZSM-(25) and E-Cat/ZSM-(75) have the same coke yield of 4%, while E-Cat/ZSM-(50) has slightly higher coke yield (4.7%). Overall, all the synthesized mesoporous ZSM-5 zeolites have coke yield in the range of 4%, which may be utilized in heat regeneration during combustion in the FCC regenerator.

Mesoporous ZSM-5 zeolites with Si/Al ratios 25, 50, and 75 were synthesized using a fast aging method of stirring of precursors solution at 40° C., and their activity was compared with that of commercial ZSM-5 additive (ZSM-5 (COM)) for the cracking of low-density polyethylene (LDPE) dissolved in heavy vacuum gas oil (HVGO). The fast aging of precursors solution and variation of Si/Al ratio resulted in ZSM-5 of different morphologies, crystal sizes, textural properties, and acidity. Both conversion and gas yields showed an increasing trend with an increase in loading of LDPE from 2.5 to 10 wt. % for cracking reaction over E-Cat. Similarly, the addition of ZSM-5 additive increased the yield of light olefins—in particular $C_2$-$C_4$ olefins—significantly in all the feedstocks due to the shape selectivity of ZSM-5. The mesoporous E-Cat/ZSM-5(50) gives higher conversion (83.7%) of 2.5 wt. % LDPE/HVGO and light olefin selectivity than E-Cat/ZSM-5(COM), while E-Cat/ZSM-5(75) gives a conversion of 81% with highest light olefin yield of 38.4%. The ZSM-5(75) has more strong acid sites (0.107 mmol/g) that cracked further the naphtha range to light olefins, and its optimum pore dimension hindered diffusion of the naphtha range product out of the zeolite internal cavity, thus exposing them to the strong acid sites for selective cracking to light olefins. Given that the E-Cat/ZSM-5(75) yields more light olefins—in particular $C_2$-$C_4$ olefins—than all the studied catalysts, the synthesized mesoporous ZSM-5(75) is considered an excellent ($C_2$-$C_4$) olefins-boosting additive and could be a good option in the FCC process for the co-cracking of HVGO and plastic waste mixture, under typical FCC cracking conditions.

Numerous modifications and variations of the present disclosure are possible in light of the above teachings. It is, therefore, to be understood that within the scope of the appended claims, the invention may be practiced otherwise than as specifically described herein.

The invention claimed is:

1. A process for producing $C_2$-$C_4$ olefins, comprising:
fluid catalytic cracking a solution of a low density polyethylene (LDPE) in a heavy vacuum gas oil in the presence of a catalyst, wherein the catalyst comprises:
an ultra-stable Y zeolite; and,
a ZSM-5 zeolite,
wherein the ZSM-5 zeolite has:
a silica to alumina ratio by weight of from about 40:1 to about 80:1;
a mesopore surface area of from about 150 to about 250 $m^2$/g, as determined by Barrett-Joyner-Halenda (BJH) desorption analysis;
a mesopore volume of from about 0.070 to about 0.200 $cm^3$/g, as determined by Barrett-Joyner-Halenda (BJH) desorption analysis; and,
a total acidity of from about 0.25 to about 0.75 mmol/g, as determined by ammonia temperature programmed desorption.

2. The process according to claim 1, wherein the fluid catalytic cracking comprises:
fluidizing a stream of the solution of the low density polyethylene (LDPE) in the heavy vacuum gas oil in a riser reactor;
cracking the solution stream with the catalyst in the riser reactor to produce a cracked stream and spent catalyst; and,
separating the cracked stream and the spent catalyst in a separator.

3. The process according to claim 2, wherein the weight hourly velocity of the stream of the solution of the low density polyethylene (LDPE) in the heavy vacuum gas oil is from about 1 to about 20 hr$^{-1}$.

4. The process according to claim 1, wherein the solution of the low density polyethylene (LDPE) in the heavy vacuum gas oil comprises from about 1 to about 15 wt. % of the low density polyethylene (LDPE), based on the total weight of the solution.

5. The process according to claim 1, wherein the solution of the low density polyethylene (LDPE) in the heavy vacuum gas oil comprises from about 2 to about 15 wt. % of the low density polyethylene (LDPE), based on the total weight of the solution.

6. The process according to claim 1, wherein the solution of the low density polyethylene (LDPE) in the heavy vacuum gas oil has a density of from about 0.85 to about 0.95 g/cm$^3$.

7. The process according to claim 1, wherein the solution of the low density polyethylene (LDPE) in the heavy vacuum gas oil has a density of from about 0.89 to about 0.91 g/cm$^3$.

8. The process according to claim 1, wherein the solution of the low density polyethylene (LDPE) in the heavy vacuum gas oil has, based on the weight of the solution:

a carbon content of from about 85 to about 90 wt. %; and, a hydrogen content of from about 10 to about 15 wt. %.

9. The process according to claim 1, wherein the solution of the low density polyethylene (LDPE) in the heavy vacuum gas oil has:

a sulfur content of from about 4000 to about 6000 parts per million by weight; and, a nitrogen content of from about 150 to about 250 parts per millions by weight.

10. The process according to claim 1, wherein the fluid catalytic cracking is performed at a temperature of from about 500 to about 700° C.

11. The process according to claim 1, wherein the fluid catalytic cracking is performed at a temperature of from about 550 to about 650° C.

12. The process according to claim 1, wherein the ratio by weight of the catalyst to the solution is from about 3:1 to about 9:1.

13. The process according to claim 1, wherein the ratio by weight of the catalyst to the solution is from about 4:1 to about 6:1.

14. The process according to claim 1, wherein the catalyst comprises, based on the total weight of the catalyst:

from about 80 to about 95 wt. % of the ultra-stable Y zeolite; and, from about 5 to about 20 wt. % of the ZSM-5 zeolite.

15. The process according to claim 1, wherein the catalyst comprises, based on the total weight of the catalyst:

from about 80 to about 90 wt. % of the ultra-stable Y zeolite; and, from about 10 to about 20 wt. % of the ZSM-5 zeolite.

16. The process according to claim 1, wherein the ZSM-5 zeolite has a surface area of from about 300 to about 400 m$^2$/g, as determined by Brunauer-Emmett-Teller (BET) analysis.

17. The process according to claim 1, wherein the ZSM-5 zeolite has, as determined by Barrett-Joyner-Halenda (BJH) desorption analysis:

a mesopore surface area of from about 175 to about 250 m$^2$/g; and, a mesopore volume of from about 0.075 to about 0.200 cm$^3$/g.

18. The process according to claim 1, wherein the ZSM-5 zeolite has a median pore diameter of from about 2 to about 6 nm, as determined by Barrett-Joyner-Halenda (BJH) desorption analysis.

19. The process according to claim 1, wherein the ZSM-5 zeolite has a Si/Al atomic ratio of 50 (ZSM-5(50)).

20. The process according to claim 1, wherein the ZSM-5 zeolite has a Si/Al atomic ratio of 75 (ZSM-5(75)).

* * * * *